United States Patent
Jeong et al.

(10) Patent No.: US 9,627,634 B2
(45) Date of Patent: Apr. 18, 2017

(54) HETEROCYCLIC COMPOUND AND ORGANIC LIGHT-EMITTING DIODE INCLUDING THE SAME

(71) Applicant: SAMSUNG DISPLAY CO., LTD., Yongin, Gyeonggi-Do (KR)

(72) Inventors: Eun-Jae Jeong, Yongin (KR); Seok-Hwan Hwang, Yongin (KR); Young-Kook Kim, Yongin (KR); Hye-Jin Jung, Yongin (KR); Jun-Ha Park, Yongin (KR); Eun-Young Lee, Yongin (KR); Jong-Woo Kim, Yongin (KR); Jin-O Lim, Yongin (KR); Sang-Hyun Han, Yongin (KR); Kwang-Hyun Kim, Yongin (KR); Soo-Yon Kim, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 358 days.

(21) Appl. No.: 14/289,099

(22) Filed: May 28, 2014

(65) Prior Publication Data

US 2015/0041775 A1    Feb. 12, 2015

(30) Foreign Application Priority Data

Aug. 9, 2013   (KR) .......................... 10-2013-0094889

(51) Int. Cl.
*H01L 51/00* (2006.01)
*H01L 51/50* (2006.01)
(Continued)

(52) U.S. Cl.
CPC ........ *H01L 51/0094* (2013.01); *C07F 7/0812* (2013.01); *C09B 57/008* (2013.01);
(Continued)

(58) Field of Classification Search
None
See application file for complete search history.

(56) References Cited

U.S. PATENT DOCUMENTS

| 4,720,432 A | 1/1988 | VanSlyke et al. |
|---|---|---|
| 5,061,569 A | 10/1991 | VanSlyke et al. |

(Continued)

FOREIGN PATENT DOCUMENTS

| JP | 10-017860 A | 1/1998 |
|---|---|---|
| JP | 11-087067 A | 3/1999 |

(Continued)

OTHER PUBLICATIONS

Tang et al.; "Organic Electroluminescent Diodes"; Applied Physics Letters; vol. 51; Sep. 21, 1987; pp. 913-915.

(Continued)

*Primary Examiner* — J. L. Yang
(74) *Attorney, Agent, or Firm* — Lee & Morse, P.C.

(57) ABSTRACT

Provided is a heterocyclic compound represented by Formula 1 and an organic light-emitting diode including the same:

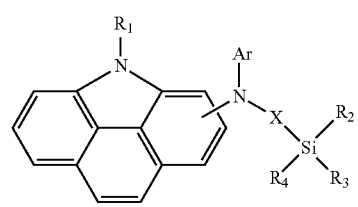

<Formula 1>

20 Claims, 1 Drawing Sheet

(51) Int. Cl.
*C07F 7/08* (2006.01)
*C09K 11/06* (2006.01)
*C09B 57/00* (2006.01)
*C09B 69/00* (2006.01)

(52) U.S. Cl.
CPC ............ *C09B 69/008* (2013.01); *C09K 11/06* (2013.01); *H01L 51/0059* (2013.01); *H01L 51/0061* (2013.01); *H01L 51/0072* (2013.01); *H01L 51/50* (2013.01); *H01L 51/5072* (2013.01); *H01L 51/5088* (2013.01); *H01L 51/5092* (2013.01); *C09K 2211/1007* (2013.01); *C09K 2211/1014* (2013.01); *H01L 51/5056* (2013.01)

(56) References Cited

U.S. PATENT DOCUMENTS

| | | | |
|---|---|---|---|
| 5,645,948 | A | 7/1997 | Shi et al. |
| 7,429,372 | B2 | 9/2008 | Pez et al. |
| 2009/0019768 | A1 | 1/2009 | Toseland et al. |
| 2010/0155714 | A1 | 6/2010 | Seo et al. |
| 2012/0211733 | A1 | 8/2012 | Hwang et al. |

FOREIGN PATENT DOCUMENTS

| | | |
|---|---|---|
| JP | 2004-083507 A | 3/2004 |
| KR | 10-0525408 B1 | 10/2005 |
| KR | 10-0573137 B1 | 4/2006 |

OTHER PUBLICATIONS

Adachi et al.; "Confinement of Charge Carriers and Molecular Excitons Within 5nm Thick Emitter Layer in Organic Electroluminescent Devices with a Double Heterostructure"; Applied Physics Letters; vol. 57; Aug. 6, 1990; pp. 531-533.

Johansson et al.; "Solid-State Amplified Spontaneous Emission in Some Spiro-Type Molecules: A New Concept for the Design of Solid-State Lasing Molecules"; vol. 10 No. 14; 1998; pp. 1136-1141.

Sakamoto et al.; "Synthesis, Characterization, and Electron-Transport Property of Perfluorinated Phenylene Dendrimers"; American Chemical Society; vol. 122 No. 8; Feb. 15, 2000; pp. 1832-1833.

Tao et al.; "Sharp Green Electroluminescence From 1H-Pyrazolo [3m 40b] Quinoline-Based Light-Emitting Diodes"; Applied Physics Letters; vol. 77 No. 11; Sep. 11, 2000; pp. 1575-1577.

Yamaguchi et al.; "Diphenylamino-Substituted 2, 5-Diarylsiloles for Single-Layer Organic Electroluminescent Devices"; Chemistry Letters 2001; The Chemical Society of Japan; Institute for Chemical Research; Kyoto University; pp. 98-99.

Hall; "A Novel Conjugated Polymer Based on 4H-Benzo[def]Carbazole Backbone for OLED"; 2009 Fall Assembly and Symposium; vol. 34 No. 2; Oct. 8, 2009-Oct. 9, 2009.

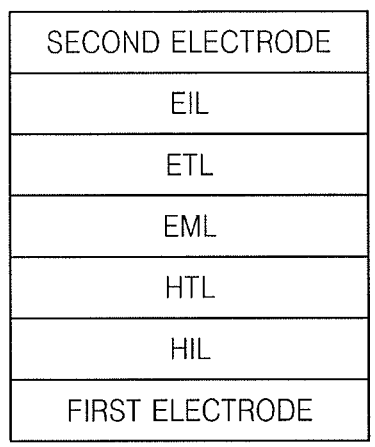

HETEROCYCLIC COMPOUND AND ORGANIC LIGHT-EMITTING DIODE INCLUDING THE SAME

CROSS-REFERENCE TO RELATED APPLICATION

Korean Patent Application No. 10-2013-0094889, filed on Aug. 9, 2013, in the Korean Intellectual Property Office, and entitled: "Heterocyclic Compound and Organic Light-Emitting Diode Including The Same," is incorporated by reference herein in its entirety.

BACKGROUND

1. Field

One or more embodiments relate to a heterocyclic compound and an organic light-emitting diode including the same.

2. Description of the Related Art

Organic light-emitting diodes (OLEDs), which are self-emitting diodes, may have wide viewing angles, excellent contrast, quick response, high brightness, excellent driving voltage characteristics, and can provide multicolored images.

SUMMARY

Embodiments may be realized by providing a heterocyclic compound represented by Formula 1 below:

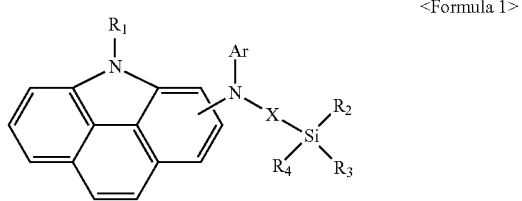

<Formula 1> wherein $R_1$ to $R_4$ are each independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_2$-$C_{60}$ heteroaryl group, a substituted or unsubstituted $C_6$-$C_{60}$ aryloxy group, or a substituted or unsubstituted $C_6$-$C_{60}$ arylthio group;

Ar is a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; and X is a single bond, a substituted or unsubstituted $C_6$-$C_{60}$ arylene group, a substituted or unsubstituted $C_2$-$C_{60}$ heteroarylene group, or a substituted or unsubstituted $C_6$-$C_{60}$ condensed polycyclic group, or a divalent linking group in which at least two of the arylene group, the heteroarylene group, and the condensed polycyclic group are connected.

Embodiments are directed to an organic light-emitting diode including a first electrode; a second electrode; and an organic layer disposed between the first electrode and the second electrode, the organic layer including the heterocyclic compound above.

Embodiments are also directed to a flat panel display device including the organic light-emitting diode above, wherein the first electrode of the organic light-emitting diode is electrically connected to a source electrode or a drain electrode of a thin-film transistor.

BRIEF DESCRIPTION OF THE DRAWING

Features will become apparent to those of skill in the art by describing in detail exemplary embodiments with reference to the attached drawings in which:

FIG. 1 illustrates a schematic view of a structure of an organic light-emitting diode (OLED) according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. As used herein, the term "and/or" includes any and all combinations of one or more of the associated listed items. Expressions such as "at least one of," when preceding a list of elements, modify the entire list of elements and do not modify the individual elements of the list.

According to an aspect, there is provided an organic light-emitting diode (OLED) including a compound represented by Formula 1 below:

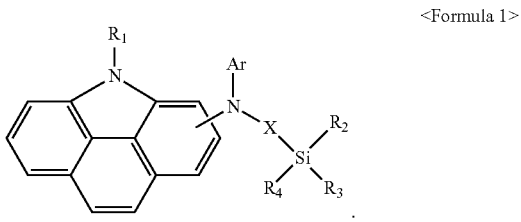

<Formula 1>

$R_1$ to $R_4$ may each independently be a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryloxy group, a substituted, a substituted or unsubstituted $C_2$-$C_{60}$ heteroaryl group, a substituted or unsubstituted $C_6$-$C_{60}$ aryloxy group, a substituted a substituted or unsubstituted $C_6$-$C_{60}$ arylthio group;

Ar may be a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; and X may be a single bond, a substituted or unsubstituted $C_6$-$C_{60}$ arylene group, a substituted or unsubstituted $C_2$-$C_{60}$ heteroarylene group, or a substituted or unsubstituted $C_6$-$C_{60}$ condensed polycyclic group, or a divalent linking group in which at least two of the arylene group, the heteroarylene group, and the condensed polycyclic group are connected.

Hereinafter, definitions of representative substituents used herein will now be described in detail.

According to another embodiment, $R_1$ of Formula 1 above may be represented by Formula 2a or Formula 2b below:

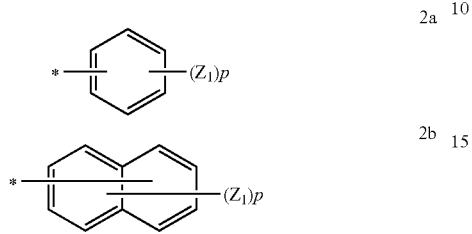

In Formula 2a or Formula 2b, $Z_1$ may be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group, wherein $Z_1$ may be different from or identical to each other when there is a plurality of $Z_1$s;

p is an integer from 1 to 7; and

* indicates a binding site.

According to another embodiment, Ar of Formula 1 above may be represented by one of Formulae 3a to 3c below:

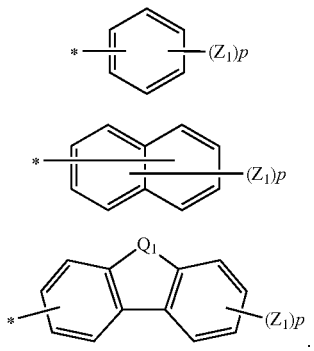

In Formulae 3a to 3c, $Q_1$ may be —$CR_{11}R_{12}$—, —$NR_{21}$—, or —O—;

$R_{11}$, $R_{12}$, $R_{21}$, and $Z_1$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group, wherein $Z_1$ may be different from or identical to each other when there is a plurality of $Z_1$s;

p is an integer from 1 to 7; and

* indicates a binding site.

According to another embodiment, X of Formula 1 above may be represented by one of Formulae 4a to 4c below:

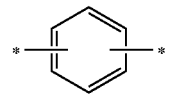

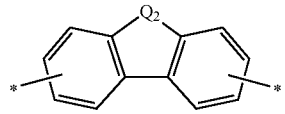

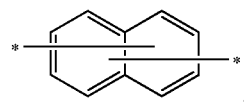

In Formulae 4a to 4c,

Q2 may be —$CR_{11}R_{12}$—, or —$NR_{21}$—;

$R_{11}$, $R_{12}$, and $R_{21}$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group; and

* indicates a binding site.

According to another embodiment, $R_2$, $R_3$, and $R_4$ of Formula 1 above may each independently be a $C_1$-$C_{10}$ alkyl group or represented by Formula 5a below:

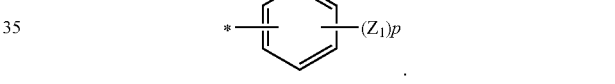

In Formula 5a, $Z_1$ may be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group, wherein $Z_1$ may be different from or identical to each other when there is a plurality of $Z_1$s;

p is an integer from 1 to 5; and

* indicates a binding site.

Hereinafter, the definition of representative substituents used herein will now be described in detail. (In this regard, numbers of carbons limiting a substituent are non-limited, and thus the substituent characteristics are not limited).

The unsubstituted $C_1$-$C_{60}$ alkyl group used herein may be linear or branched. Non-limiting examples of the unsubstituted $C_1$-$C_{60}$ alkyl group are a methyl group, an ethyl group, a propyl group, an iso-butyl group, a sec-butyl group, a pentyl group, an iso-amyl group, a hexyl group, a heptyl group, an octyl group, a nonanyl group, and a dodecyl group. At least one hydrogen atom of the unsubstituted $C_1$-$C_{60}$ alkyl group may be substituted with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_2$-$C_{16}$ heteroaryl group.

The unsubstituted $C_2$-$C_{60}$ alkenyl group indicates an unsubstituted alkyl group having at least one carbon-carbon double bond in the center or at a terminal thereof. Examples of the unsubstituted $C_2$-$C_{60}$ alkenyl group are an ethenyl group, a propenyl group, and a butenyl group. At least one hydrogen atom of the unsubstituted $C_2$-$C_{60}$ alkenyl group may be substituted with the same substituent as used in the substituted alkyl group described above.

The unsubstituted $C_2$-$C_{60}$ alkynyl group indicates an unsubstituted alkyl group having at least one carbon-carbon triple bond in the center or at a terminal of thereof. Examples of the unsubstituted $C_2$-$C_{60}$ alkynyl group are acetylene, propylene, phenylacetylene, naphthylacetylene, isopropylacetylene, t-butylacetylene, and diphenylacetylene. At least one hydrogen atom of the unsubstituted $C_2$-$C_{60}$ alkynyl group may be substituted with the same substituent as used in the substituted alkyl group described above.

The unsubstituted $C_3$-$C_{60}$ cycloalkyl group indicates an alkyl group in the form of $C_3$-$C_{60}$ rings, and at least one hydrogen atom of the unsubstituted $C_3$-$C_{60}$ cycloalkyl group may be substituted with the same substituent as used in the $C_1$-$C_{60}$ alkyl group described above.

The unsubstituted $C_1$-$C_{60}$ alkoxy group has a structure of —OA (wherein, A is an unsubstituted $C_1$-$C_{60}$ alkyl group as described above). Non-limiting examples of the unsubstituted $C_1$-$C_{60}$ alkoxy group are a methoxy group, an ethoxy group, a propoxy group, an isopropyloxy group, a butoxy group, and a pentoxy group. At least one hydrogen atom of the unsubstituted $C_1$-$C_{60}$ alkoxy group may be substituted with the same substituent as used in the substituted alkyl group described above.

The unsubstituted $C_6$-$C_{60}$ aryl group indicates a carbocyclic aromatic system including at least one ring. When the unsubstituted $C_6$-$C_{60}$ aryl group has two or more of rings, the rings may be fused or linked to each other by a single bond. The term 'aryl' refers to an aromatic system, such as phenyl, napthyl, and anthracenyl. Also, at least one hydrogen atom of the unsubstituted $C_6$-$C_{60}$ aryl group may be substituted with the same substituent as used in the $C_1$-$C_{60}$ alkyl group described above.

Examples of the substituted or unsubstituted $C_6$-$C_{60}$ aryl group are a phenyl group, a $C_1$-$C_{10}$ alkylphenyl group (e.g., an ethylphenyl group), a biphenyl group, a $C_1$-$C_{10}$ alkylbiphenyl group, a $C_1$-$C_{10}$ alkoxybiphenyl group, an o-, m-, and p-toryl group, an o-, m-, and p-cumenyl group, a mesityl group, a phenoxyphenyl group, an (α,α-dimethylbenzene)phenyl group, an (N,N'-dimethyl)aminophenyl group, an (N,N'-diphenyl)aminophenyl group, a pentalenyl group, an indenyl group, a naphtyl group, a $C_1$-$C_{10}$ alkylnaphtyl group (e.g., a methylnaphtyl group), a $C_1$-$C_{10}$ alkoxynaphtyl group (e.g., a methoxynaphtyl group), an anthracenyl group, an azulenyl group, a heptalenyl group, an acenaphtylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coroneryl group, a trinaphtylenyl group, a heptaphenyl group, a heptacenyl group, a pyranthrenyl group, and an ovalenyl group.

The unsubstituted $C_2$-$C_{60}$ heteroaryl group used herein may include one, two, three, or four hetero atoms selected from N, O, P, or S. When the unsubstituted $C_2$-$C_{60}$ heteroaryl group has two or more of rings, the rings may be fused or linked to each other by a single bond. Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indolyl group, a quinolinyl group, an isoquinolinyl group, and a dibenzothiophene group. In addition, at least one hydrogen atom of the unsubstituted $C_2$-$C_{60}$ heteroaryl group may be substituted with the same substituent as used in the unsubstituted $C_1$-$C_{60}$ alkyl group described above.

The unsubstituted $C_6$-$C_{60}$ aryloxy group is a group represented by —$OA_1$, wherein $A_1$ is a $C_6$-$C_{60}$ aryl group. An example of the unsubstituted $C_6$-$C_{60}$ aryloxy group is a phenoxy group. At least one hydrogen atom of the unsubstituted $C_6$-$C_{60}$ aryloxy group may be substituted with the same substituent as used in the unsubstituted $C_1$-$C_{60}$ alkyl group described above.

The unsubstituted $C_6$-$C_{60}$ arylthio group is a group represented by —$SA_1$, wherein $A_1$ is a $C_6$-$C_{60}$ aryl group. Examples of the unsubstituted $C_6$-$C_{60}$ arylthio group are a benzenethio group and a naphthylthio group. At least one hydrogen atom of the unsubstituted $C_6$-$C_{60}$ arylthio group may be substituted with the same substituent as used in the unsubstituted $C_1$-$C_{60}$ alkyl group described above.

The unsubstituted $C_6$-$C_{60}$ condensed polycyclic group used herein refers to a substituent including at least two rings, wherein at least one aromatic ring and/or at least one non-aromatic ring are fused to each other, or refers to a substituent having an unsaturated group in a ring that may not form a conjugated structure. Thus, the unsubstituted $C_6$-$C_{60}$ condensed polycyclic group is distinct from an aryl group or a heteroaryl group in terms of being non-aromatic.

According to another embodiment, examples of the heterocyclic compound of Formula 1 above are the compounds below:

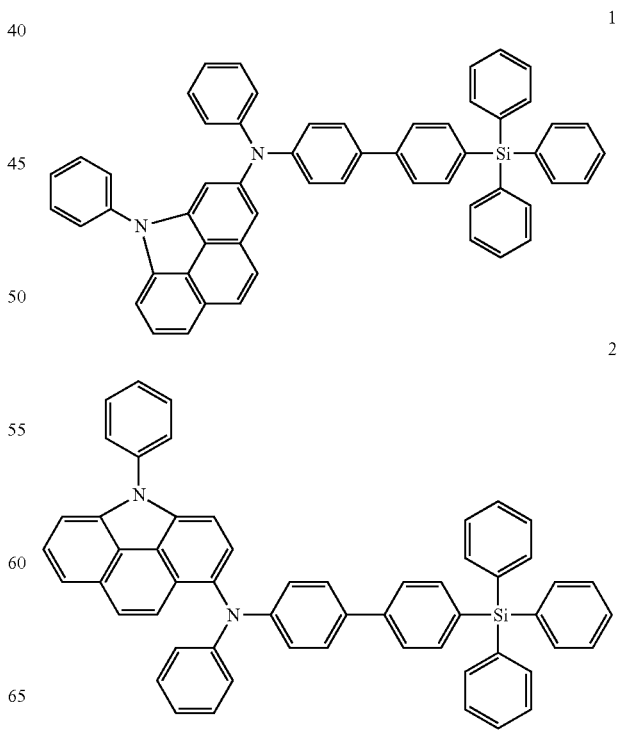

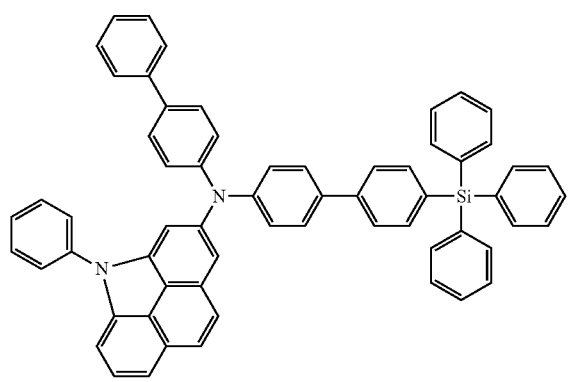
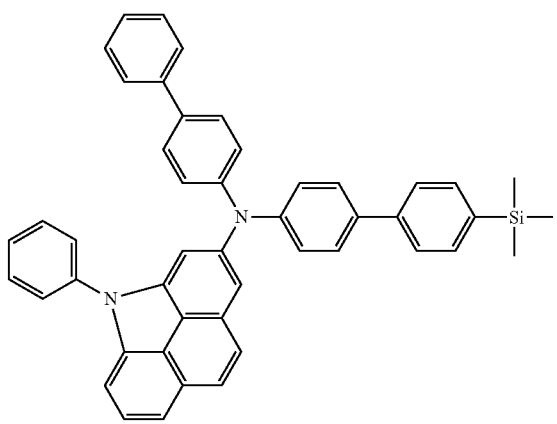

11
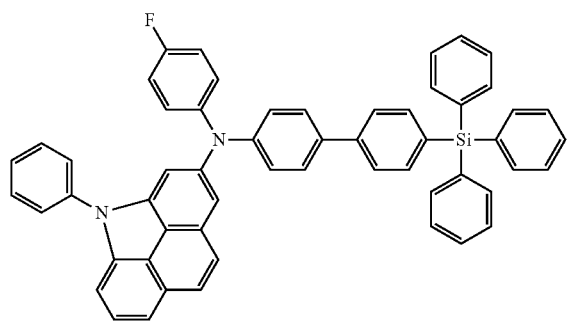
12
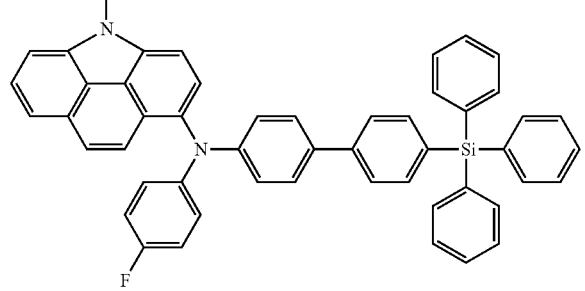
13
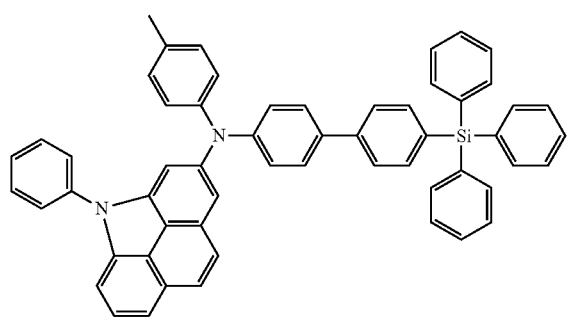
14
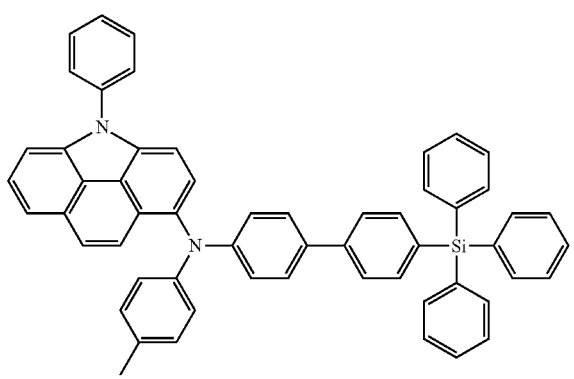
15
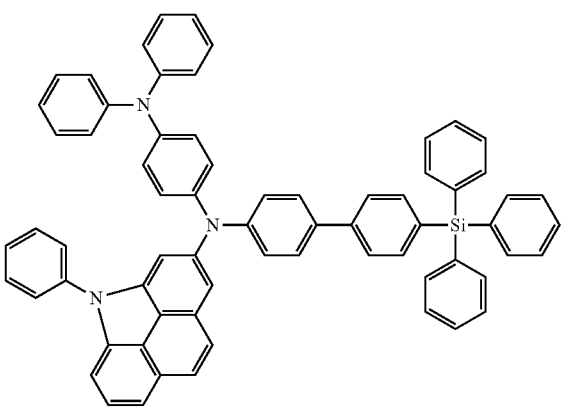
16
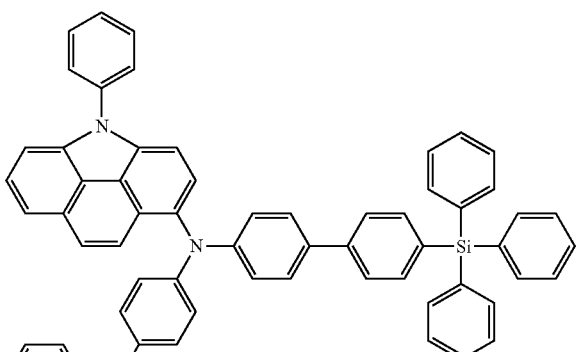
17
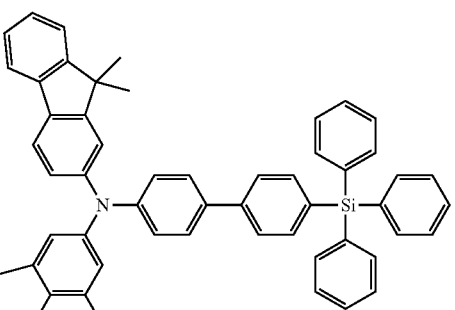

18
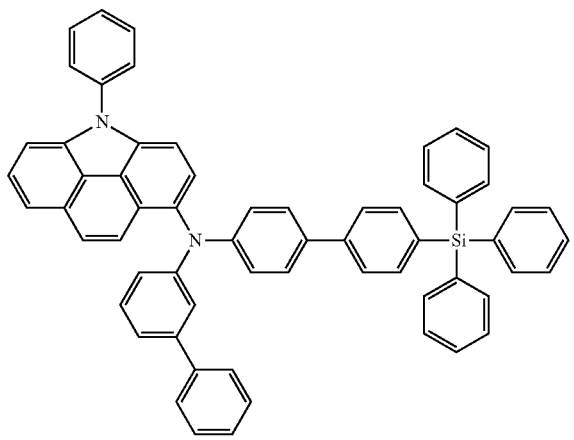
19
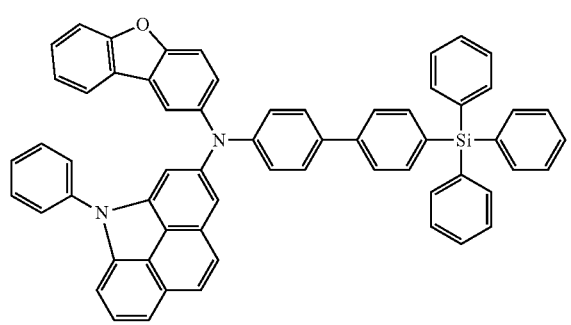
20
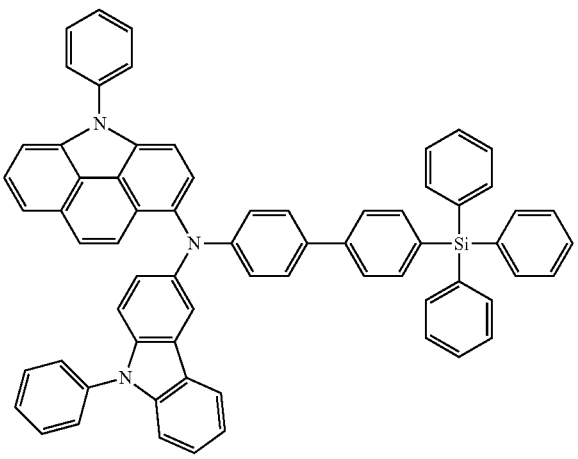
21
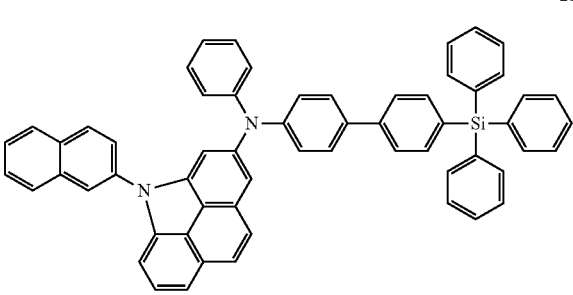
22
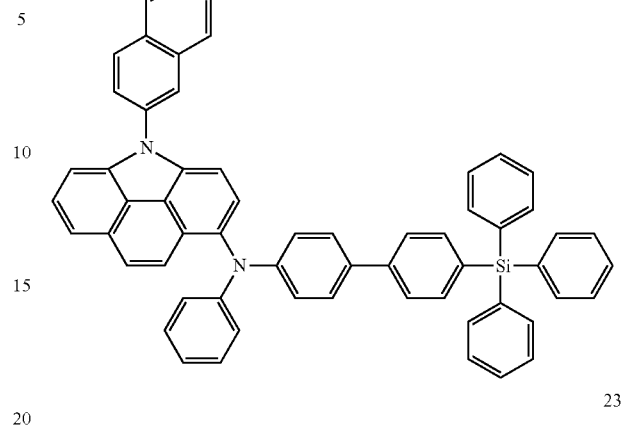
23
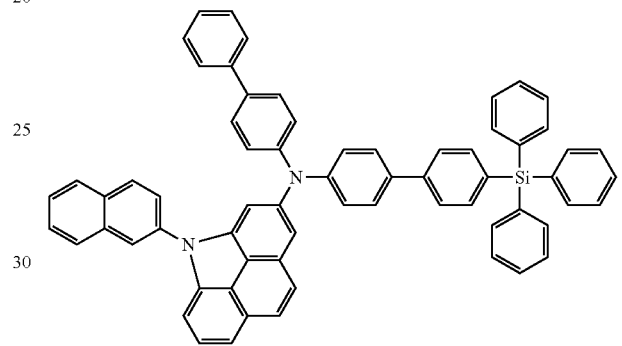
24
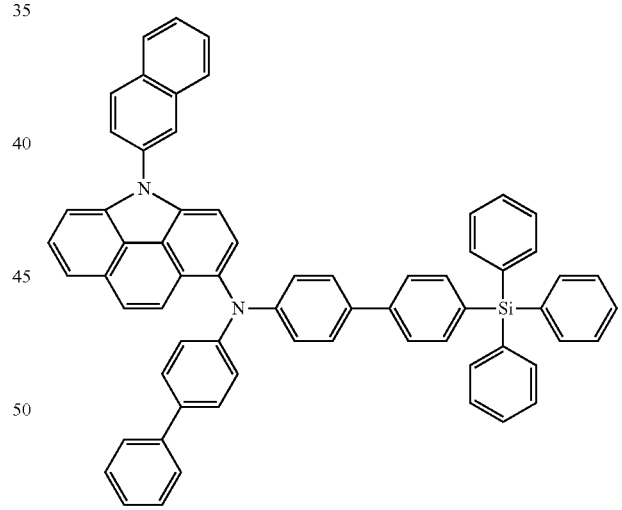
25
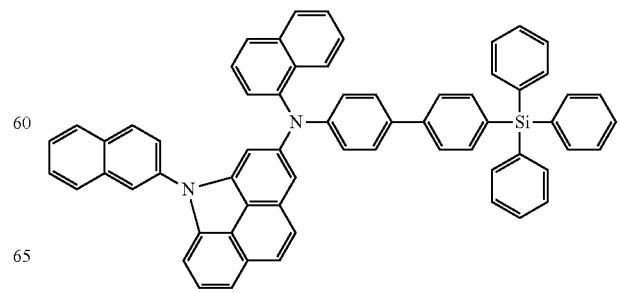

26
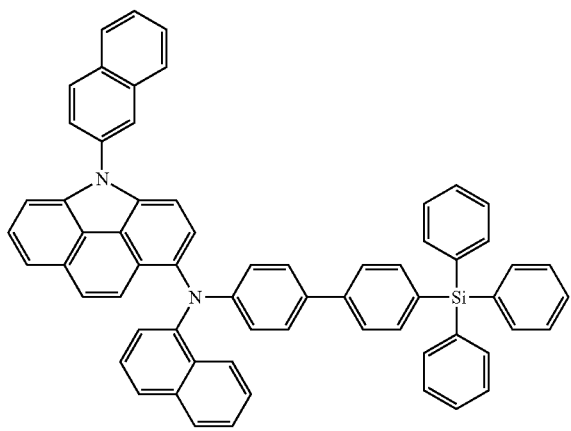
27
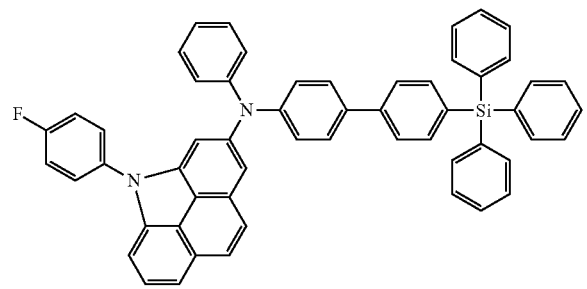
28
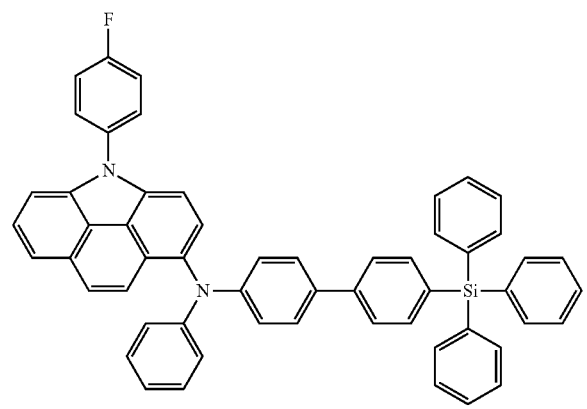
29
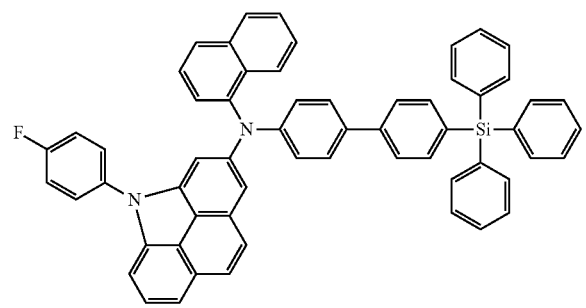
30
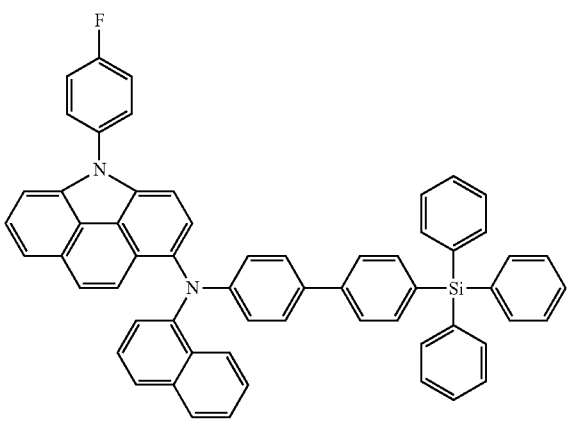
31
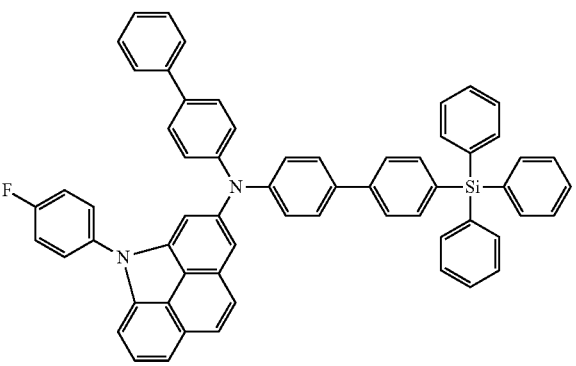
32
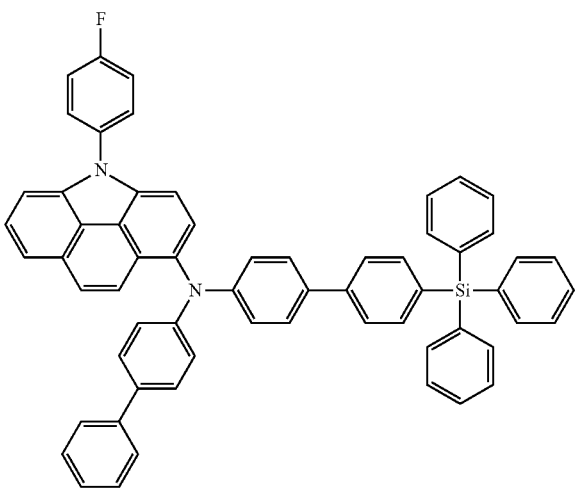
33
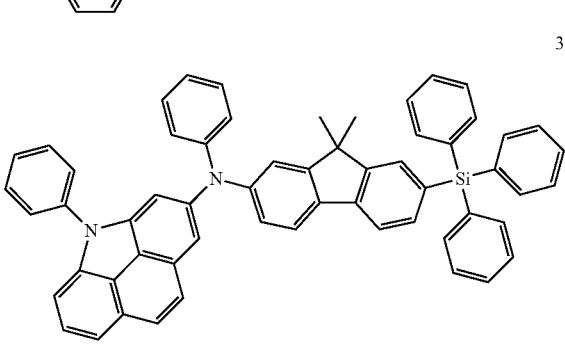

34
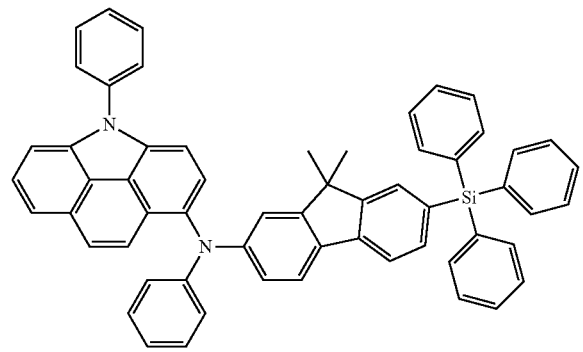
35
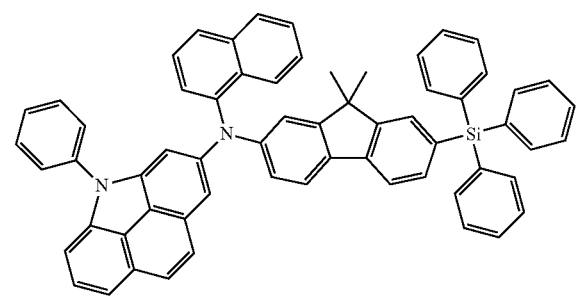
36
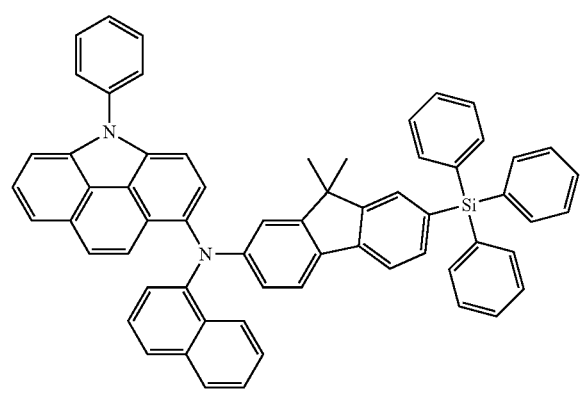
37
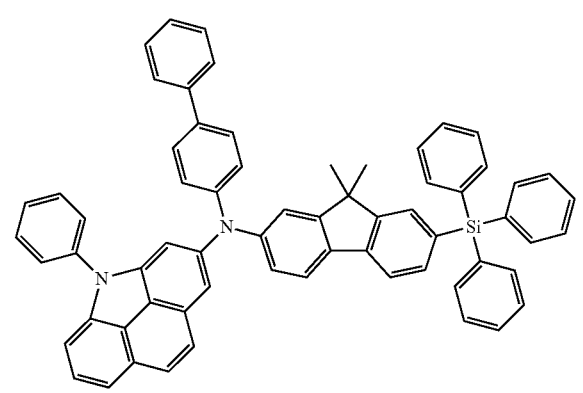
38
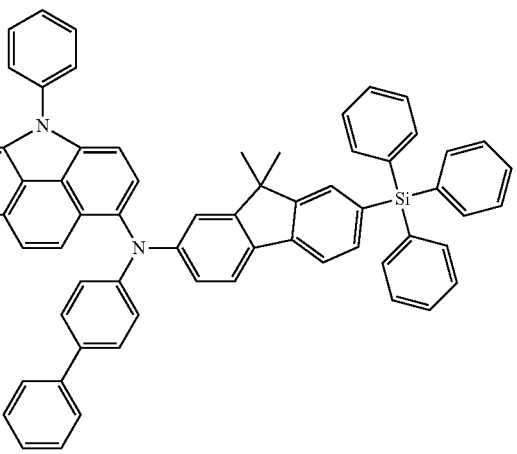
39
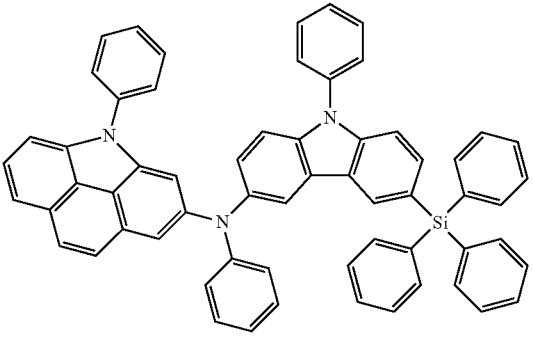
40
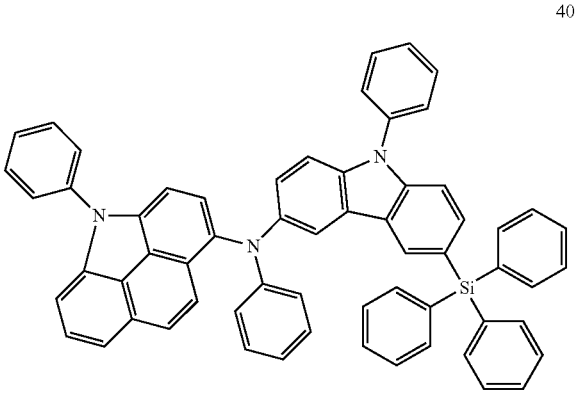

41
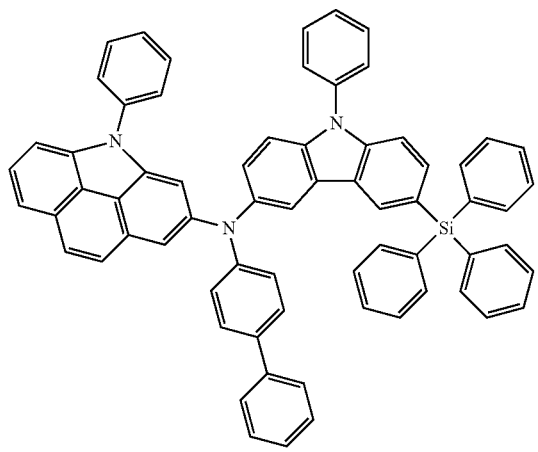
42
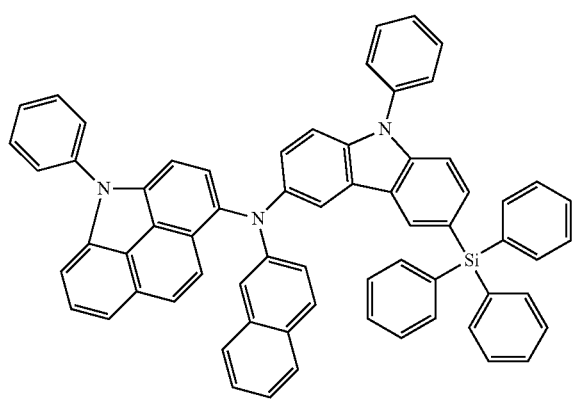
43
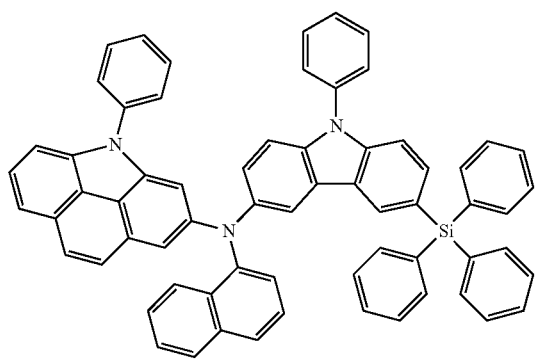
44
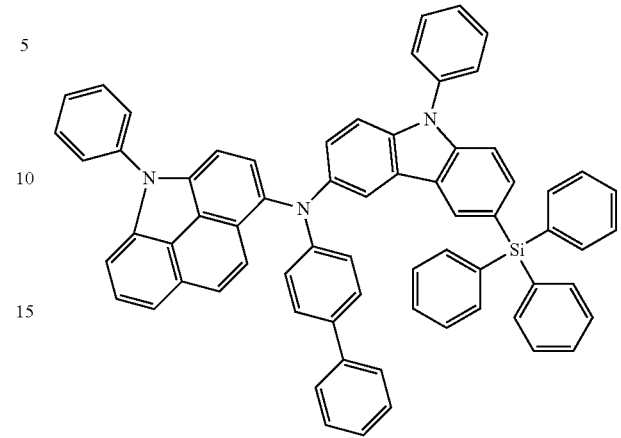
45
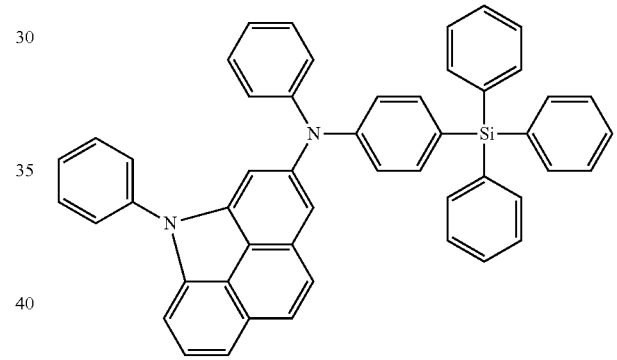
46
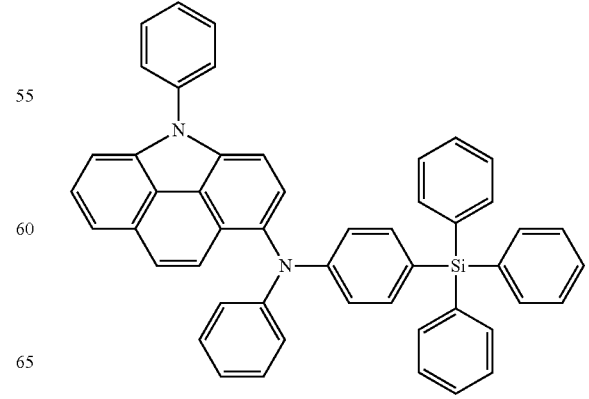

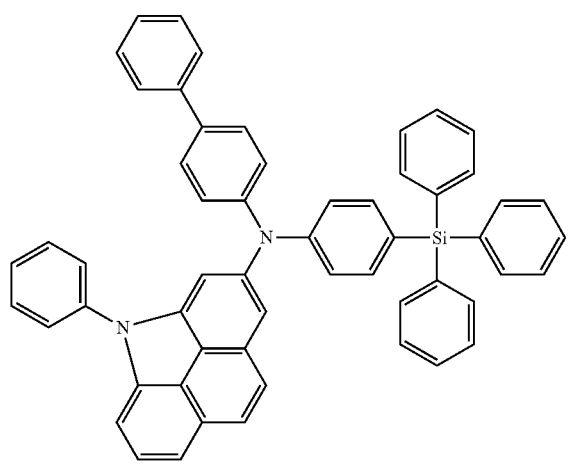
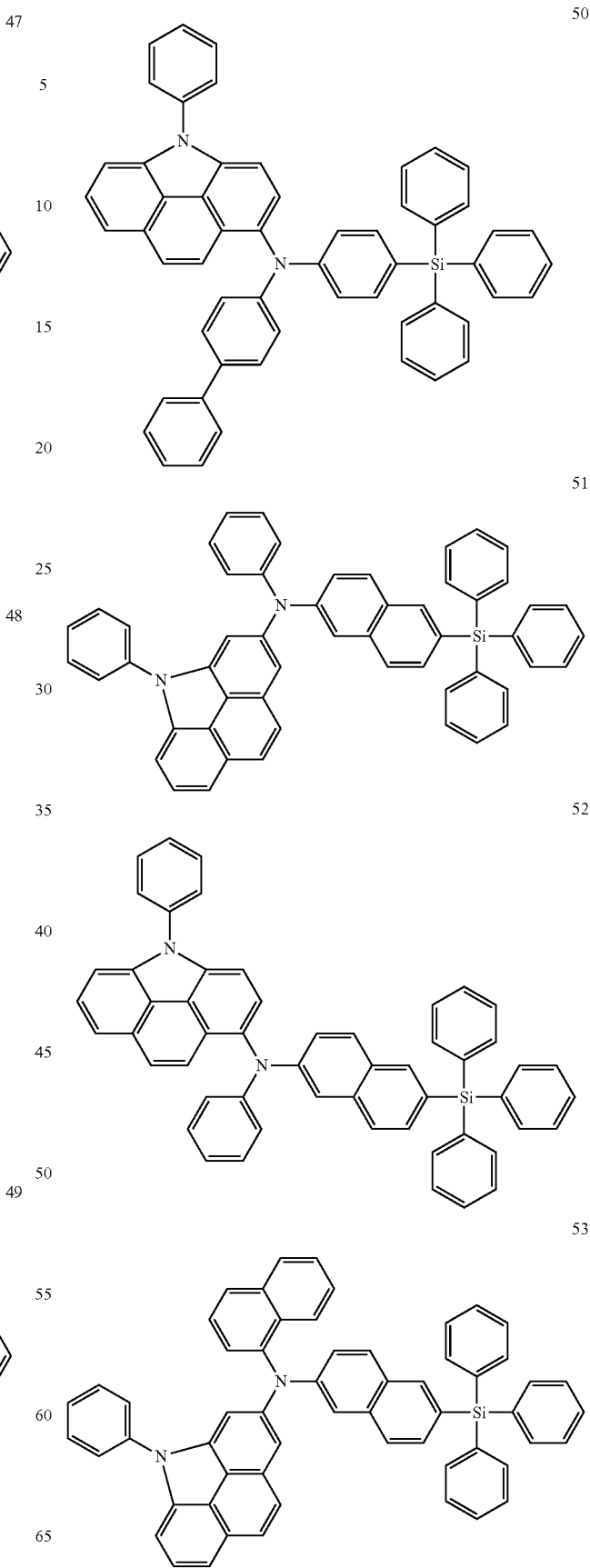

54
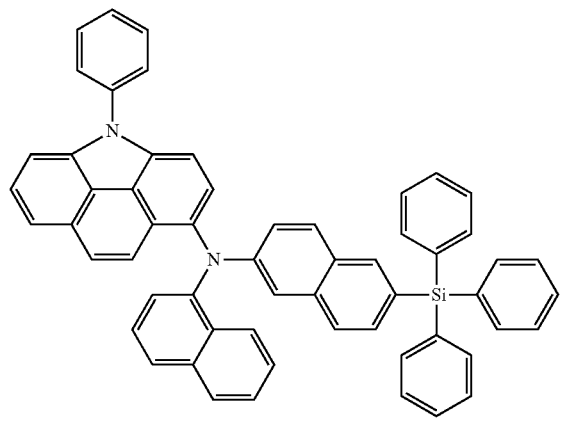
55
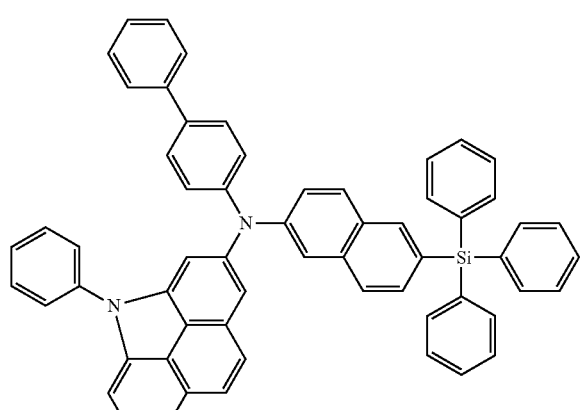
56
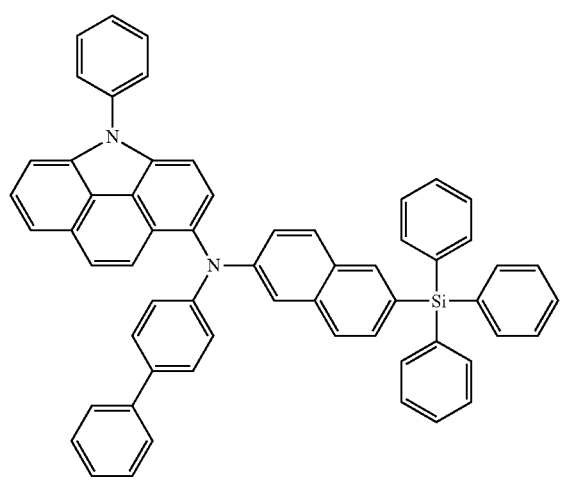
57
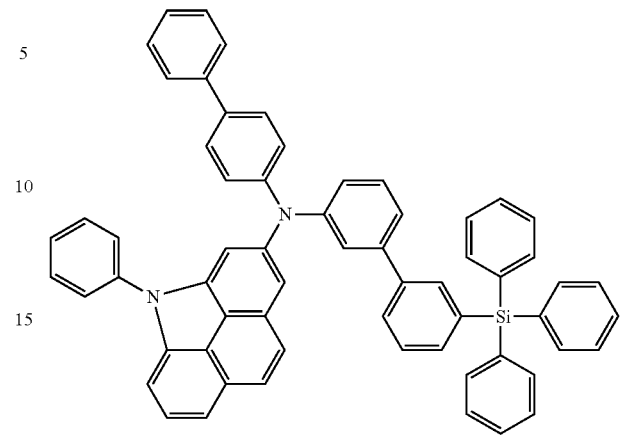
58
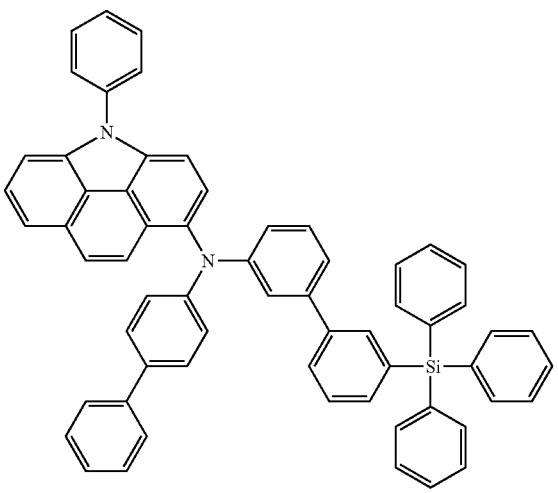
59
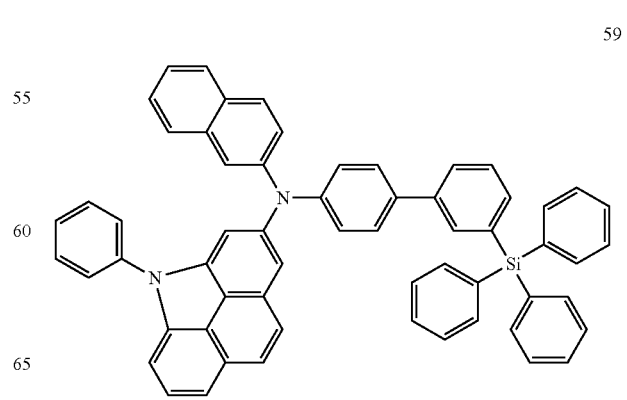

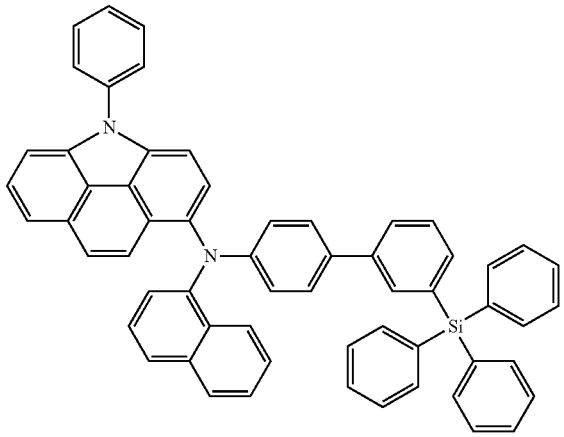

According to another aspect, an organic-light emitting diode (OLED) includes a first electrode; a second electrode; and an organic layer that is disposed between the first electrode and the second electrode, wherein the organic layer may include the heterocyclic compound of Formula 1 above.

The organic layer may include at least one layer selected from a hole injection layer (HIL), a hole transport layer (HTL), a functional layer having both hole injection and hole transport capabilities (hereinafter, referred to as a "H-functional layer"), a buffer layer, an electron blocking layer (EBL), an emission layer (EML), a hole blocking layer (HBL), an electron transport layer (ETL), an electron injection layer (EIL), and a functional layer having both electron injection and electron transport capabilities (hereinafter, referred to as an "E-functional layer").

In greater detail, the organic layer may be an HTL, an HIL, or a H-functional layer having both hole injection and hole transport capabilities.

In some other embodiments, the organic layer may include an EIL, an ETL, an E-functional layer having both electron injection and electron transport capabilities, an EML, a HIL, a HTL, or a H-functional layer having both hole injection and hole transport capabilities, wherein the EML may further include an anthracene-based compound, an arylamine-based compound, or a styryl-based compound.

In some other embodiments, the organic layer may include an EIL, an ETL, an E-functional layer having both electron injection and electron transport capabilities, an EML, a HIL, a HTL, or a H-functional layer having both hole injection and hole transport capabilities, wherein at least one layer of a red EML, a green EML, a blue EML, and a white EML of the EML may include a phosphorescent compound. The HIL, the HTL, or the H-functional layer having both hole injection and hole transport capabilities may include a charge-generating material. The charge-generating material may be a p-dopant, and the p-dopant may be a quinone derivative, a metal oxide, or a cyano group-containing compound.

According to another embodiment, the organic layer may include an ETL, and the ETL may include an electron-transporting organic compound and a metal complex. Here, the metal complex may be a lithium (Li) complex.

The term "organic layer" used herein refers to a single layer and/or a multi-layer disposed between the first electrode and the second electrode of the OLED.

FIG. 1 illustrates a schematic view of a structure of the OLED according to an embodiment. Hereinafter, a structure and a manufacturing method of the OLED according to an embodiment will be described in detail with reference to FIG. 1.

The substrate (not illustrated) may be any substrate used in an OLED, such as a glass substrate or a transparent plastic substrate with excellent mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Examples of the first electrode-forming material are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), or magnesium-silver (Mg—Ag) are used, the first electrode may be formed as a reflective electrode.

The first electrode may have a single-layer structure or a multi-layer structure including at least two layers. For example, the first electrode may have a three-layered structure of ITO/Ag/ITO.

The organic layer may be disposed on the first electrode.

The organic layer may include a HIL, a HTL, a buffer layer (not illustrated), an EML, an ETL, or an EIL.

An HIL may be formed on the first electrode by using various methods, such as vacuum deposition, spin coating, casting, and Langmuir-Blodgett (LB) deposition.

When the HIL is formed by using vacuum deposition, the vacuum deposition conditions may vary according to the compound that is used to form the HIL, and the desired structure and thermal properties of the HIL to be formed. For example, the vacuum deposition may be performed at a temperature in a range of about 100° C. to about 500° C., a pressure in a range of about $10^{-8}$ torr to about $10^{-3}$ torr, and a deposition rate in a range of about 0.01 Å/sec to about 100 Å/sec.

When the HIL is formed by using spin coating, the coating conditions may vary according to the compound that is used to form the HIL, and the desired structure and thermal properties of the HIL to be formed. For example, the coating rate may be in a range of about 2,000 to about 5,000 rpm, and a temperature at which heat treatment is performed to remove a solvent after coating may be in a range of about 80° C. to about 200° C.

The HIL may be formed of the heterocyclic compound of Formula 1 according to an embodiment, or examples of the material used to form the HIL include N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonicacid (Pani/CSA), and polyaniline/poly(4-styrenesulfonate) (PANI/PSS):

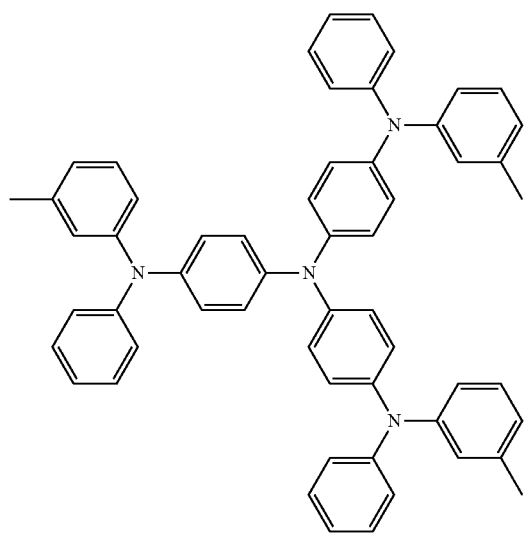

m-MTDATA

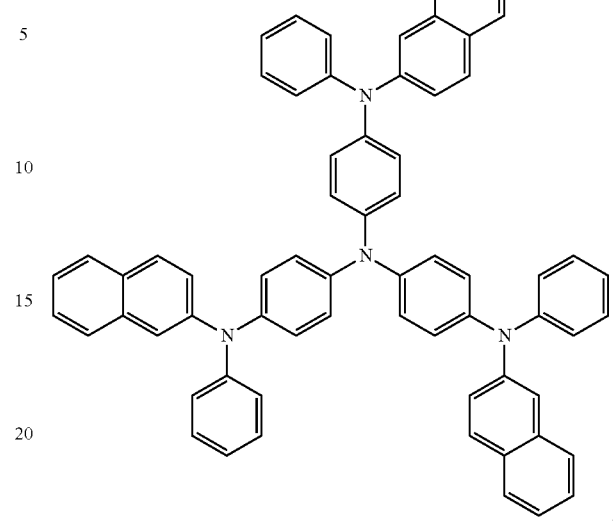

2-TNATA

A thickness of the HIL may be in a range of about 100 Å to about 10,000 Å, for example, about 100 Å to about 1,000 Å. Maintaining the thickness of the HIL within the above ranges may help provide the HIL with satisfactory hole injecting capabilities without a substantial increase in a driving voltage.

Then, an HTL may be formed on the HIL by using various methods, such as vacuum deposition, spin coating, casting, and LB deposition. When the HTL is formed by using vacuum deposition or spin coating, the deposition and coating conditions may be similar to those for the formation of the HIL, although the deposition and coating conditions may vary according to the compound that is used to form the HTL.

The HTL may be formed of the heterocyclic compound of Formula 1 according to an embodiment, or examples of the material used to form the HTL include a carbazole derivative such as N-phenylcarbazole and polyvinylcarbazole, N,N-bis (3-methylphenyl)-N,N-diphenyl-[1,1-biphenyl]-4,4'-di-amine (TPD), 4,4',4"-tris(N-carbazolyl)triphenylamine) (TCTA), and N,N'-di(1-naphthyl)-N,N'-diphenylbenzidine (NPB):

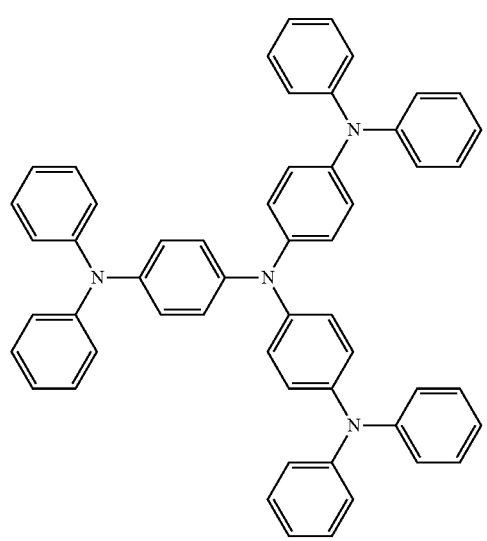

TDATA

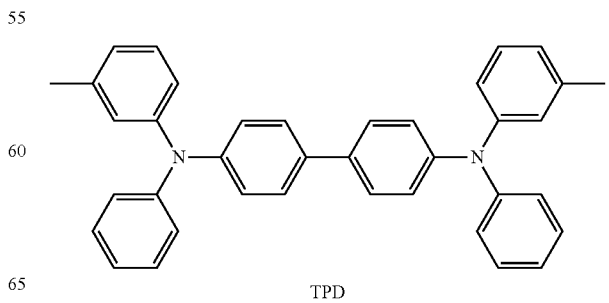

TPD

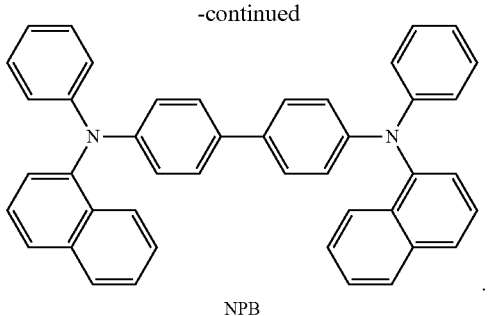

NPB

A thickness of the HTL may be in a range of about 50 Å to about 2,000 Å, for example, about 100 Å to about 1,500 Å. Maintaining the thickness of the HTL within the above ranges may help provide the HTL with satisfactory hole transporting capabilities without a substantial increase in a driving voltage.

The H-functional layer (having both hole injection and hole transport capabilities) may include at least one material selected from the above-described materials for the HIL and the HTL. A thickness of the H-functional layer may be in a range of about 500 Å to about 10,000 Å, for example, about 100 Å to about 1,000 Å. Maintaining the thickness of the H-functional layer within the above ranges may help provide the H-functional layer with satisfactory hole injecting and transporting capabilities without a substantial increase in a driving voltage.

In some other embodiments, at least one layer of the HIL, the HTL, and the H-functional layer may include at least one of compounds represented by Formulae 300 and 350 below:

<Formula 300>

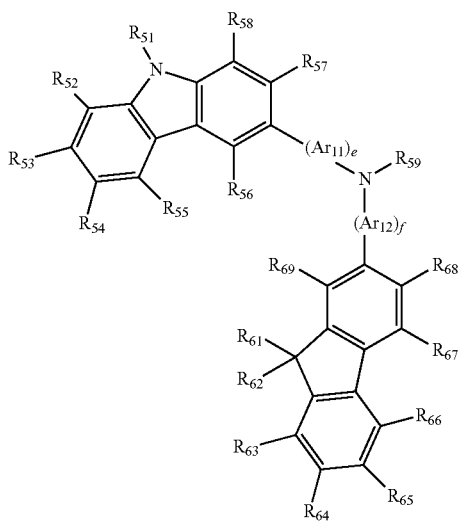

<Formula 350>

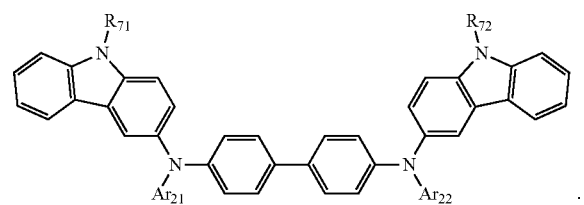

In Formulae 300 and 350, $Ar_{11}$, $Ar_{12}$, $Ar_{21}$, and $Ar_{22}$ may each independently be a substituted or unsubstituted $C_5$-$C_{60}$ arylene group.

In Formula 300, e and f may each independently be an integer from 0 to 5, for example, 0, 1, or 2. In some other embodiments, e may be 1 and f may be 0.

In Formulae 300 and 350, $R_{51}$ to $R_{58}$, $R_{61}$ to $R_{69}$, $R_{71}$, and $R_{72}$ may each independently be a hydrogen atom, a deuterium atom a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, $R_{71}$, and $R_{72}$ may each independently be a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (e.g., a methyl group, an ethyl group, a propyl group, a butyl group, a pentyl group, and a hexyl group); a $C_1$-$C_{10}$ alkoxy group (e.g., a methoxy group, an ethoxy group, a propoxy group, a butoxy group, and a pentoxy group); a $C_1$-$C_{10}$ alkyl group and a $C_1$-$C_{10}$ alkoxy group, each substituted with at least one substituent selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group, each substituted with at least one substituent selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be a phenyl group; a naphthyl group; an anthryl group;

a biphenyl group; a pyridyl group; and a phenyl group, a naphthyl group, an anthryl group, a biphenyl group, and a pyridyl group, each substituted with at least one substituent selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

According to another embodiment, the compound of Formula 300 may be a compound represented by Formula 300A below:

<Formula 300A>
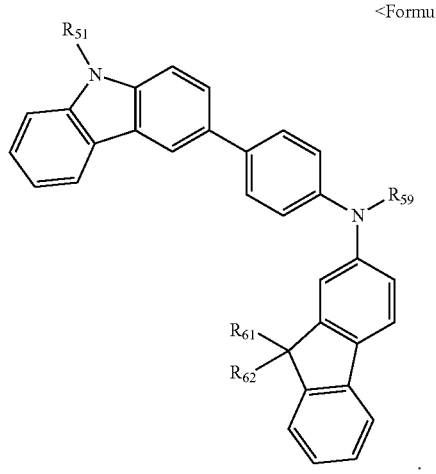
In Formula 300A, $R_{51}$, $R_{61}$, $R_{62}$, and $R_{59}$ may be as defined above.
For example, at least one layer of the HIL, HTL, and the H-functional layer may include at least one of Compounds 301 to 320:
301
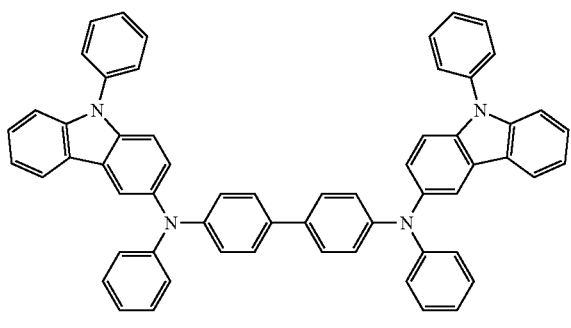
302
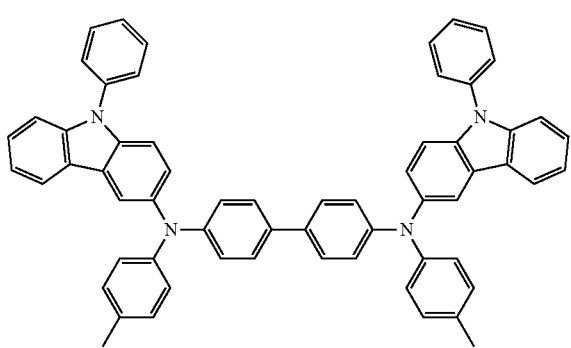
303
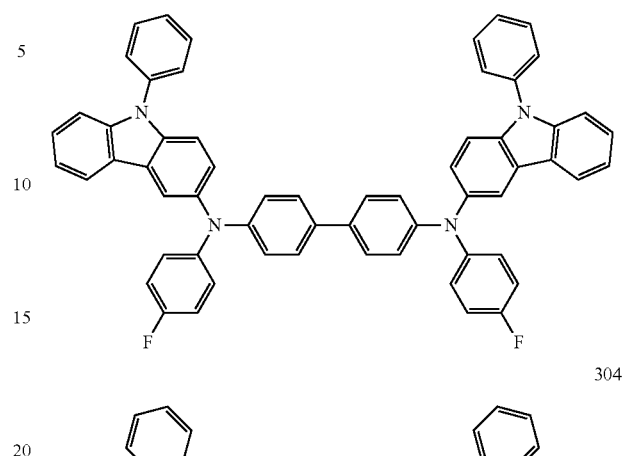
304
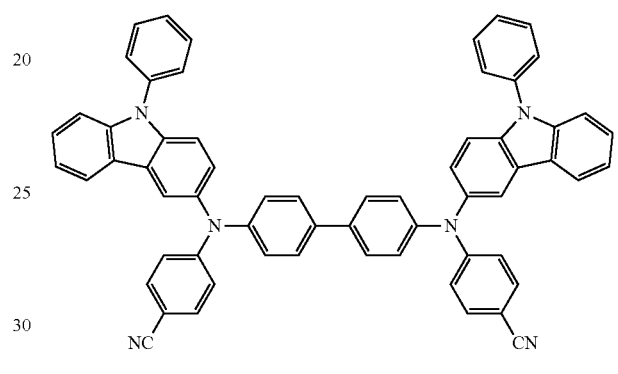
305
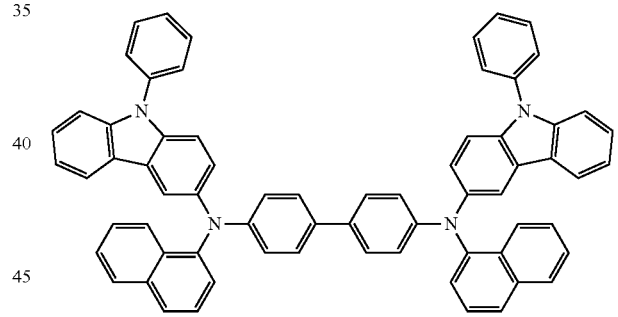
306
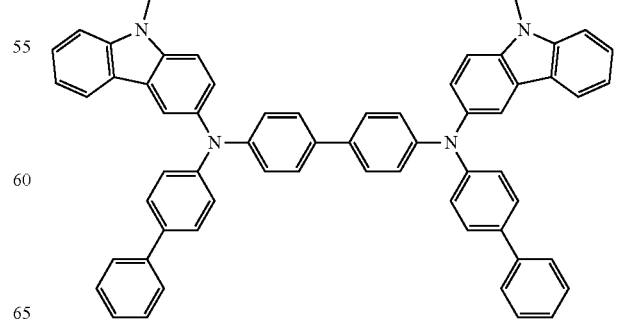

307
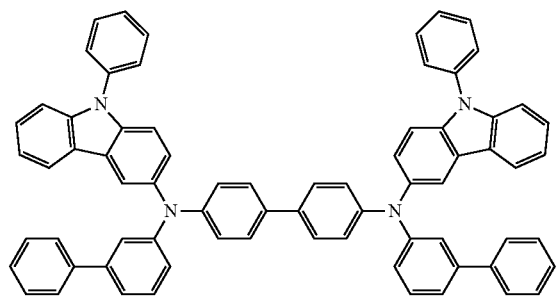
308
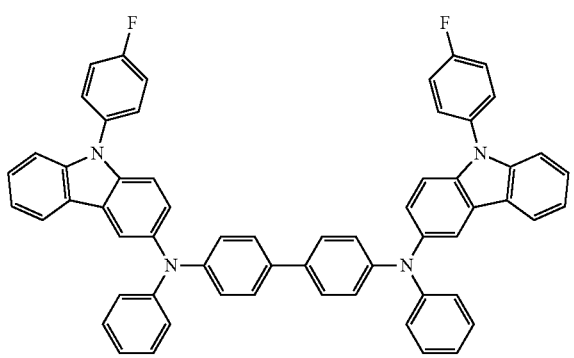
309
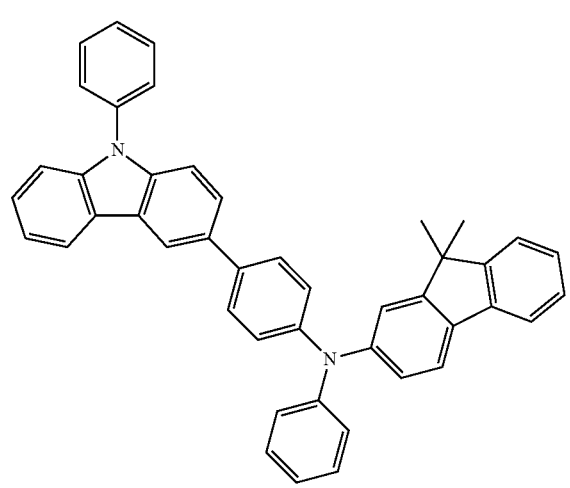
310
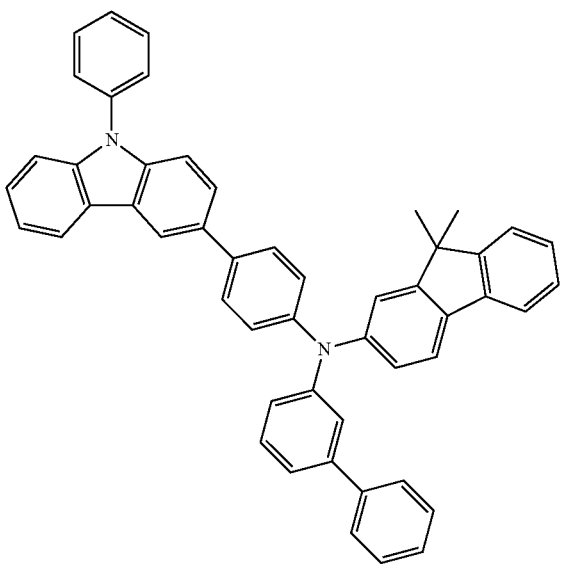
311
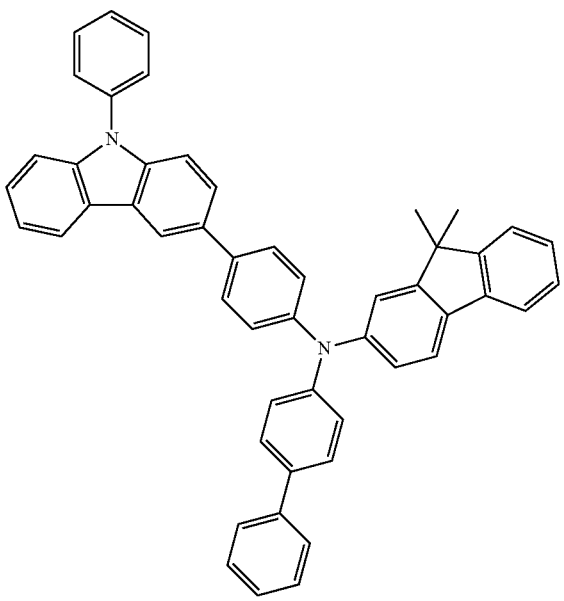

312
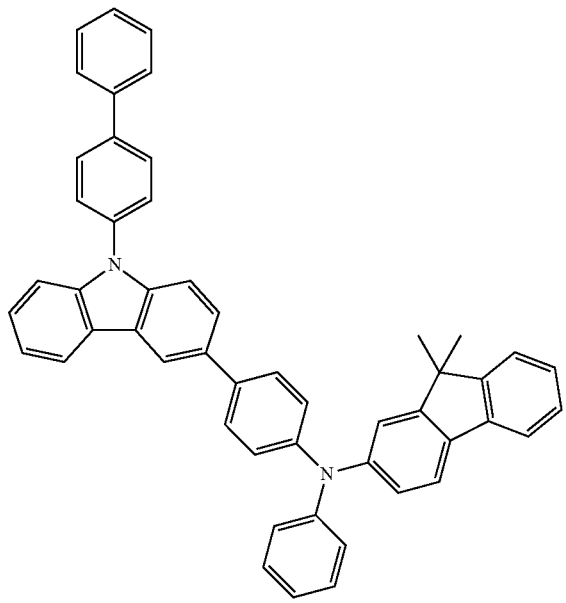
314
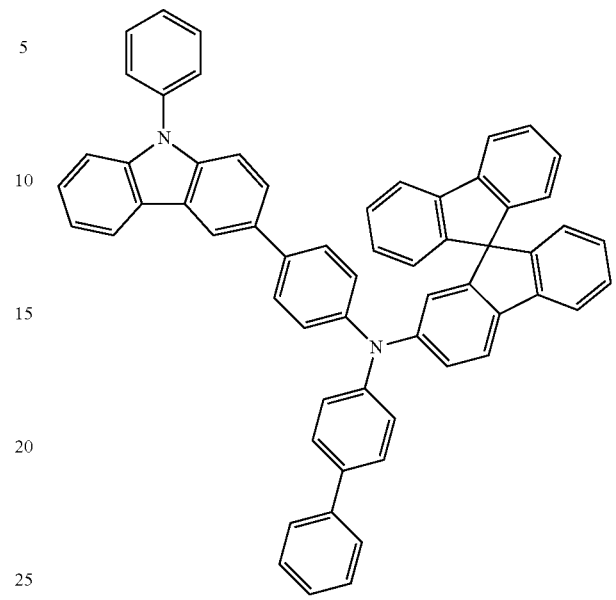
313
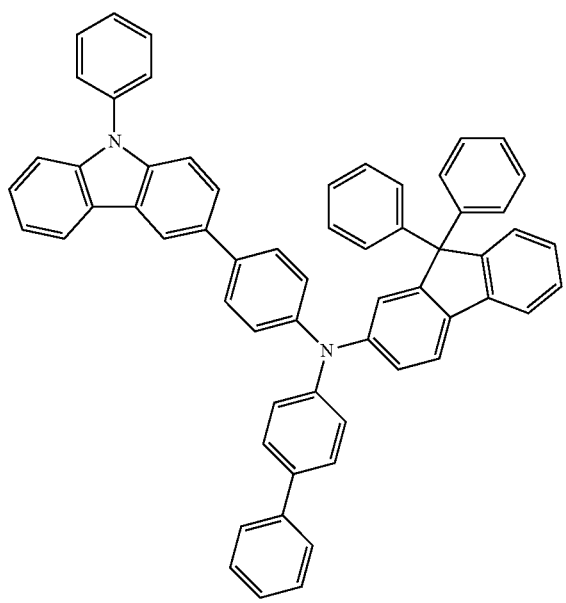
315
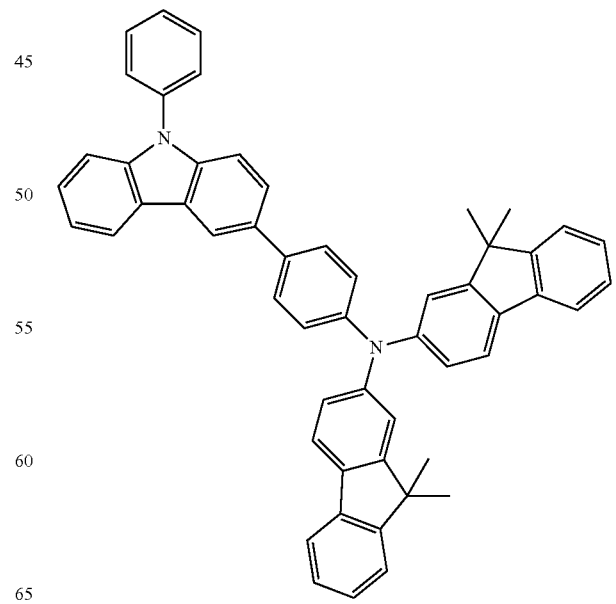

316

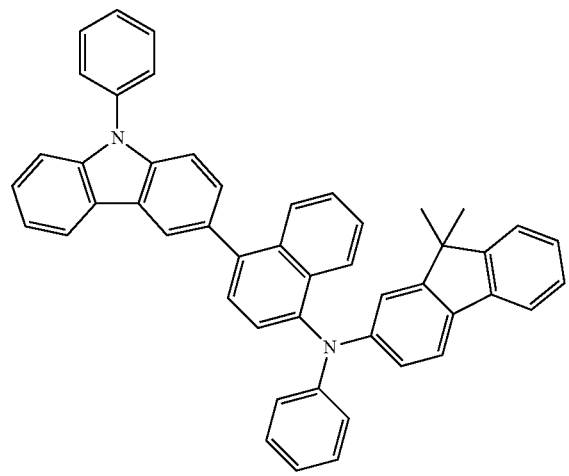

317

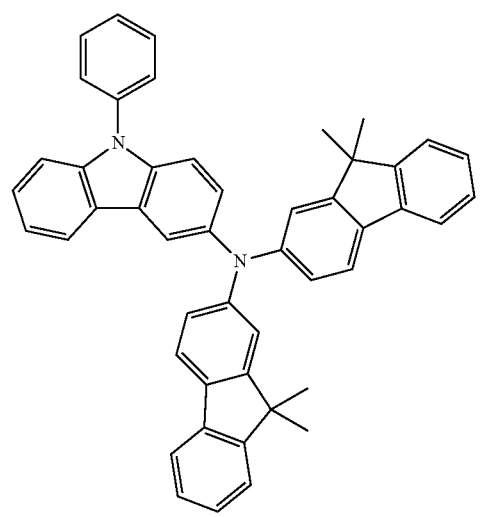

318

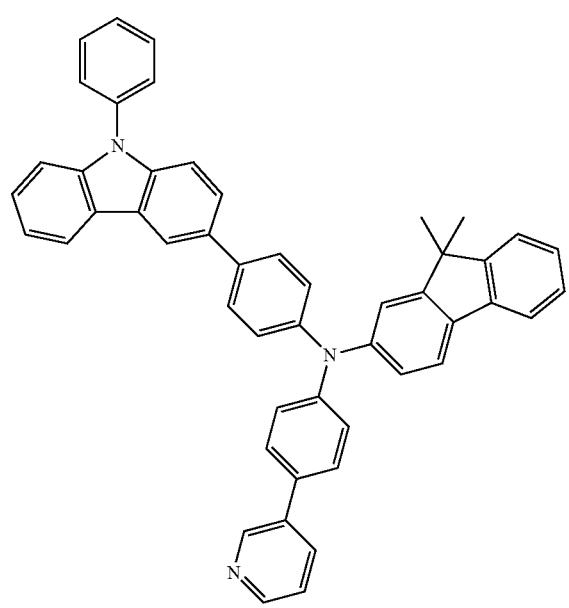

319

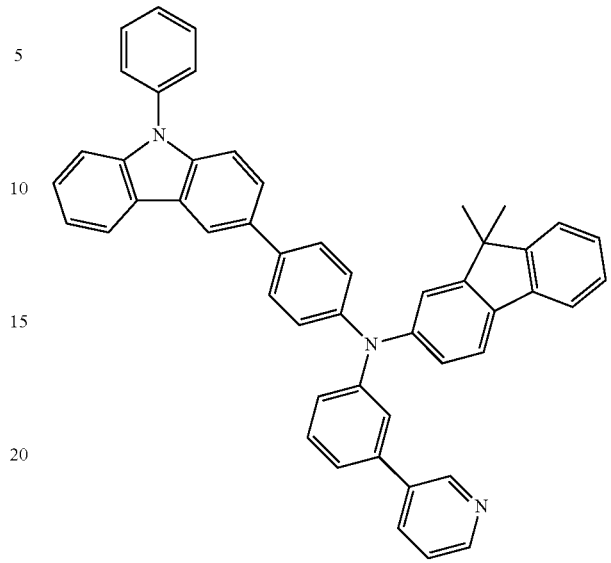

320

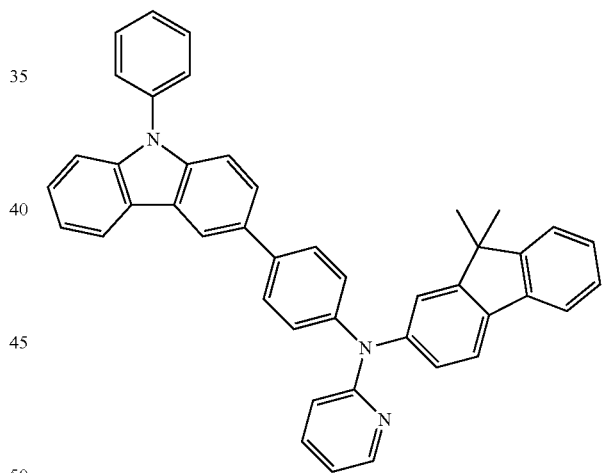

At least one layer of the HIL, HTL, and the H-functional layer may further include a charge-generating material in addition to hole-injecting materials, hole-transporting materials, and/or H-functional materials having both hole injection and hole transport capabilities, to improve conductivity of a film.

The charge-generating material may be, for example, a p-dopant. The p-dopant may be one of quinone derivatives, metal oxides, and cyano group-containing groups. Examples of the p-dopant include quinone derivatives such as tetracyanoquinodimethane (TCNQ) and 2,3,5,6-tetrafluoro-tetracyano-1,4-benzoquinodimethane (F4-TCNQ); metal oxides such as a tungsten oxide and a molybdenym oxide; and cyano group-containing compound such as Compound 200 below:

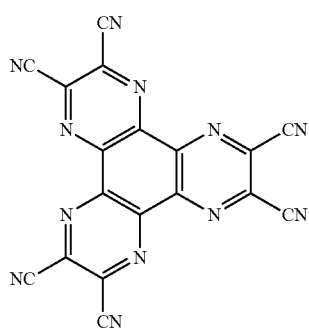

<Compound 200>

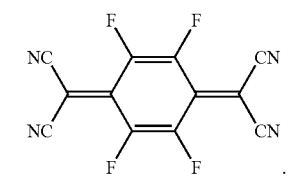

<F4-TCNQ>

When the HIL, the HTL, or the H-functional layer further includes the charge-generating material, the charge-generating material may be homogeneously dispersed or non-homogeneously distributed throughout the above-described layers.

A buffer layer may be disposed between at least one of the HIL, HTL, and the H-functional layer, and the EML. The buffer layer may compensate for an optical resonance distance of light according to a wavelength of the light emitted from the EML, and may increase efficiency. The buffer layer may include any hole injecting material or hole transporting material. In some other embodiments, the buffer layer may include the same material as one of the materials included in the HIL, the HTL, and the H-functional layer that underlie the buffer layer.

Then, an EML may be formed on the HIL, the H-functional layer, or the buffer layer by vacuum deposition, spin coating, casting, or LB deposition. When the EML is formed by using vacuum deposition or spin coating, the deposition and coating conditions may be similar to those for the formation of the HIL, although the conditions for deposition and coating may vary according to the compound that is used to form the EML.

The EML may be formed by using a variety of light-emitting materials, for example, a host and a dopant. In an embodiment, both a fluorescent dopant and a phosphorescent dopant may be used.

Examples of the host include Alq$_3$, 4,4'-N,N'-dicarbazole-biphenyl (CBP), poly(n-vinylcarbazole) (PVK), 9,10-di(naphthylene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (see Formula below), and Compounds 501 to 509 below:

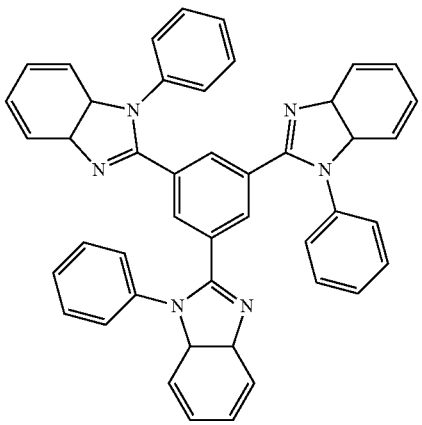

TPBI

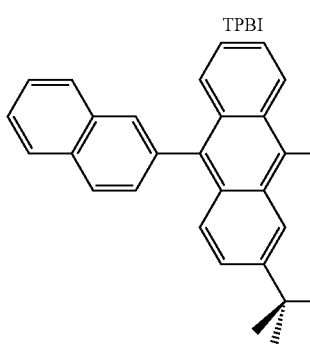

TBADN

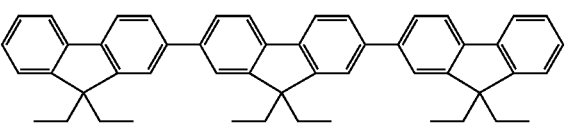

E3

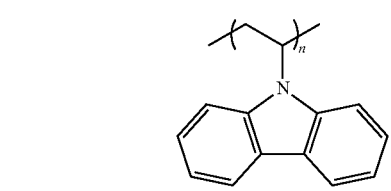

PVK

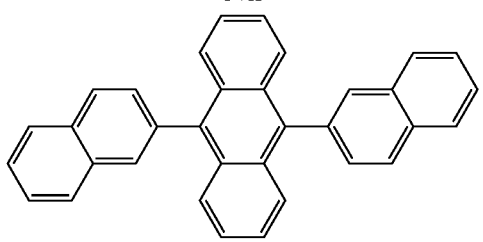

ADN

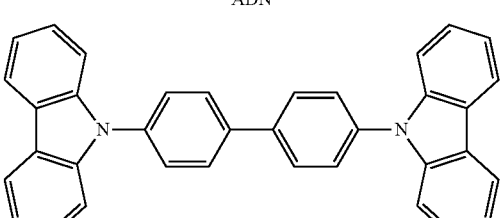

CBP

-continued
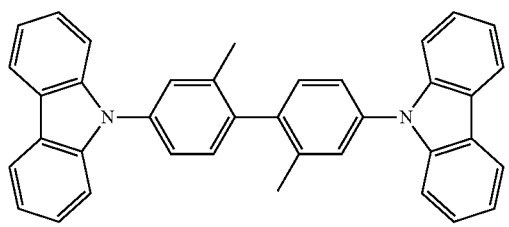
dmCBP
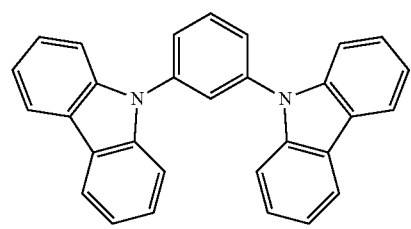
501
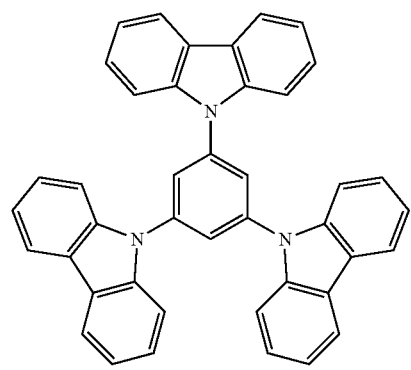
502
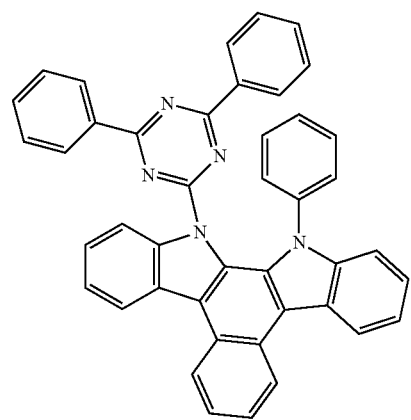
503
-continued
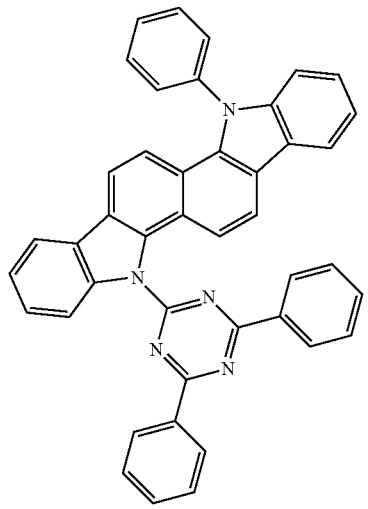
504
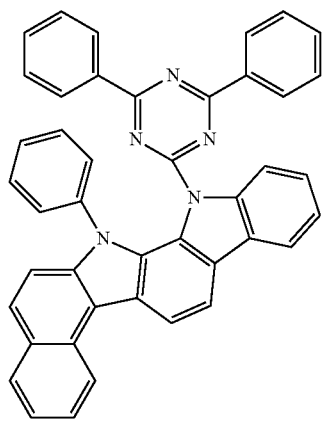
505
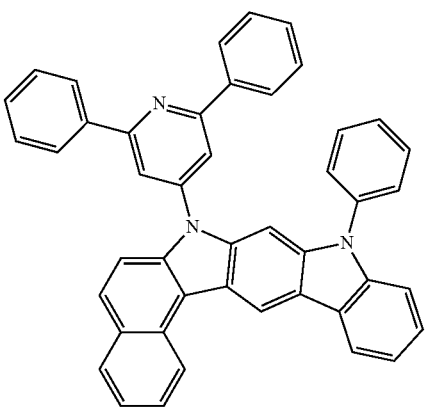
506

507

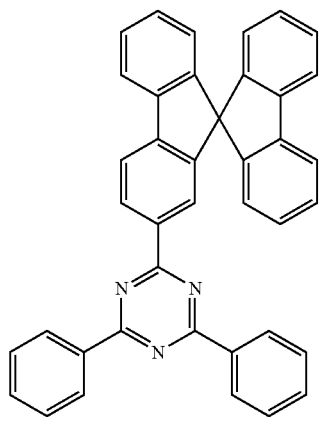

508

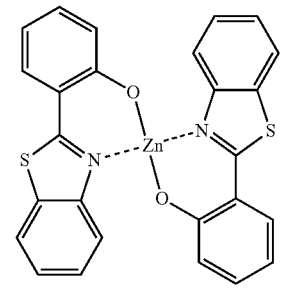

509

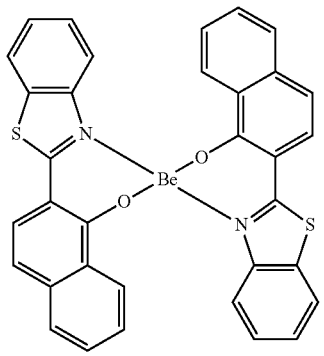

In some other embodiments, an anthracene-based compound represented by Formula 400 below may be used as the host:

<Formula 400>

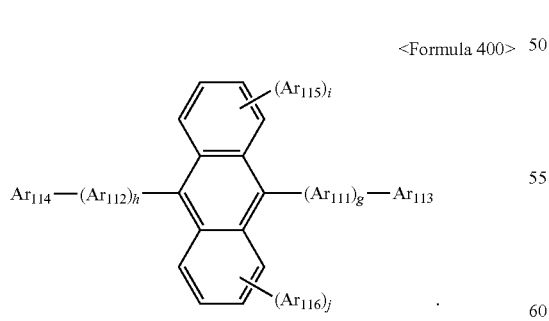

In Formula 400 above, $Ar_{111}$ and $Ar_{112}$ may each independently be a substituted or unsubstituted $C_5$-$C_{60}$ arylene group; $Ar_{113}$ to $Ar_{116}$ may each independently be a substituted or unsubstituted $C_1$-$C_{10}$ alkyl group, or a substituted or unsubstituted $C_5$-$C_{60}$ aryl group; g, h, I, and j may each independently be an integer from 0 to 4.

In some other embodiments, in Formula 400 above, $Ar_{111}$ and $Ar_{112}$ may each independently be a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one substituent selected from a phenyl group, a naphthyl group, and an anthryl group.

In Formula 400 above, g, h, I, and j may each independently be 0, 1, or 2.

In Formula 400 above, $Ar_{113}$ to $Ar_{116}$ may each independently be a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group, each substituted with at least one substituent selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

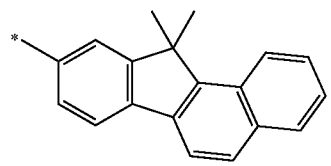

In some embodiments, the anthracene-based compound of Formula 400 above may be one of compounds represented by Formulae below:

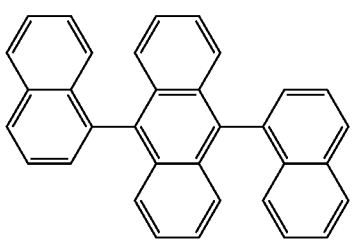

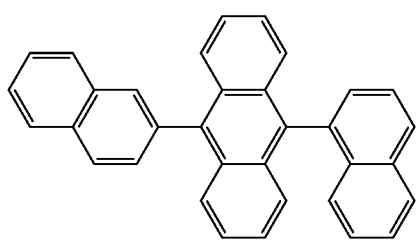

-continued
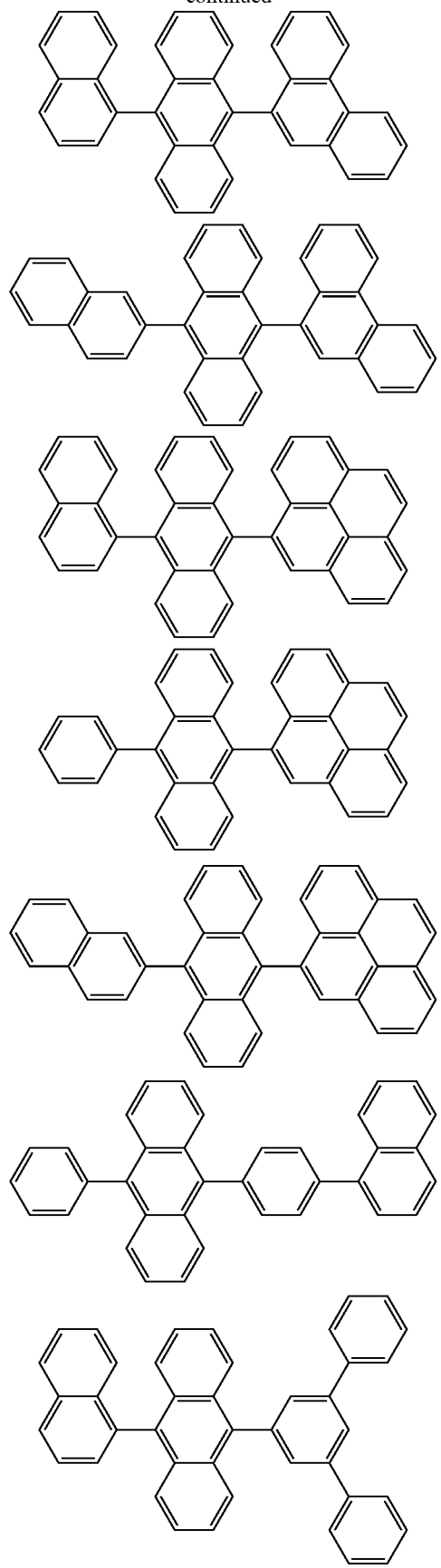
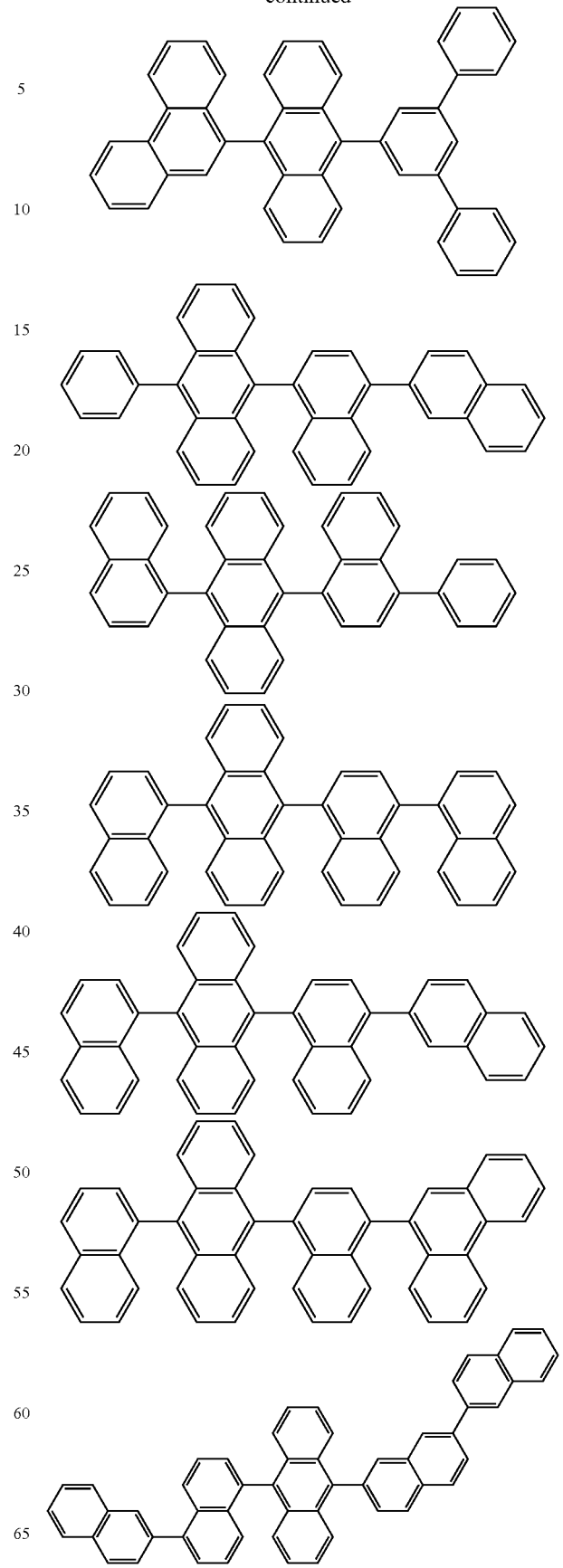

-continued
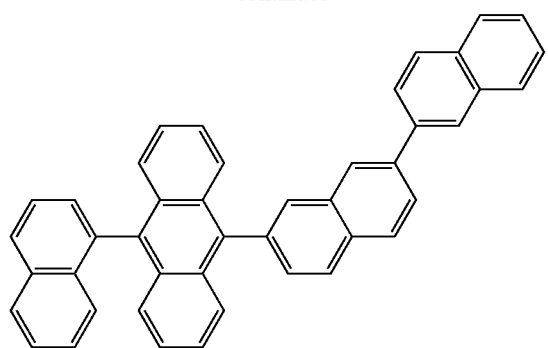
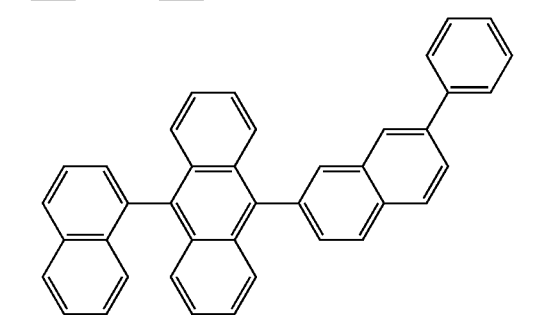
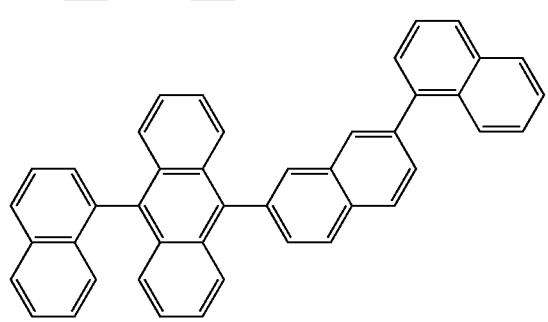
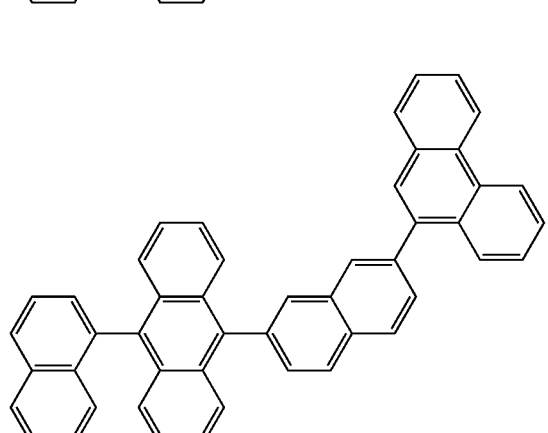
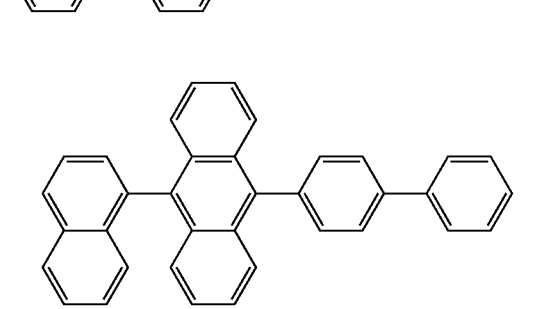
-continued
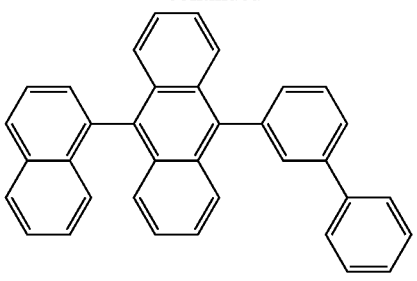
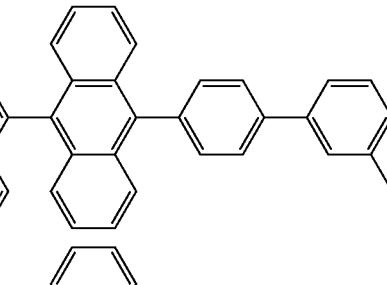
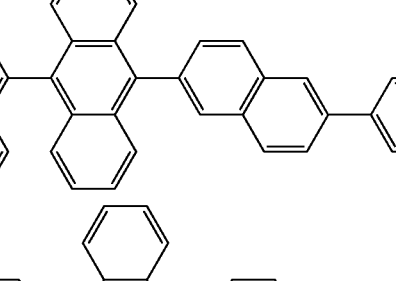
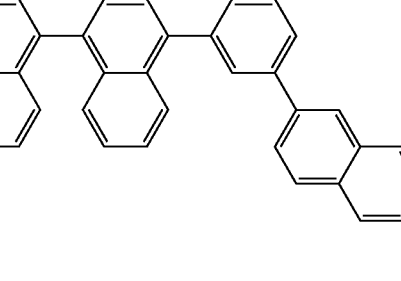
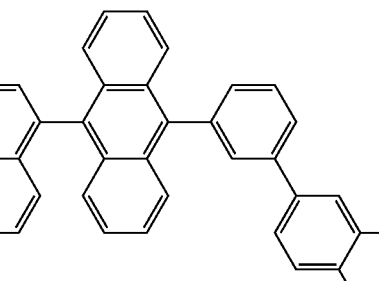
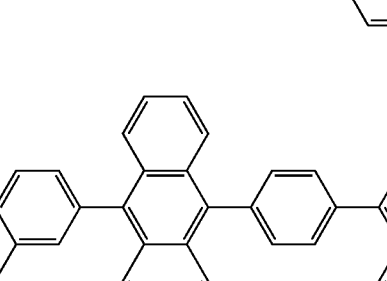

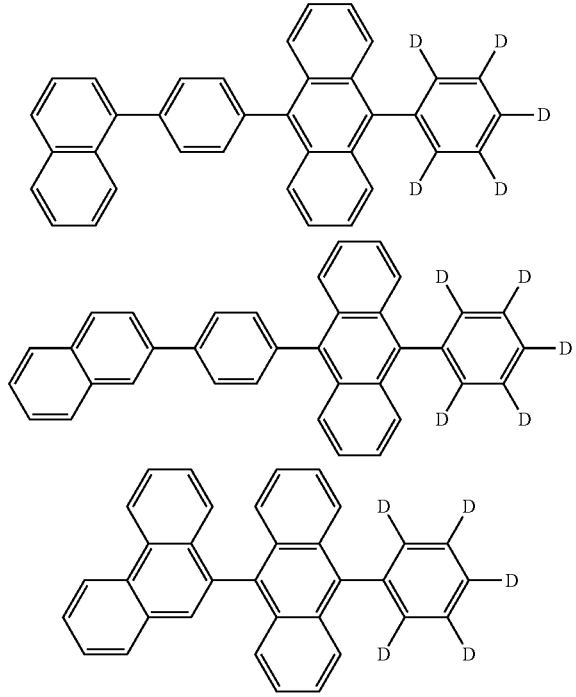
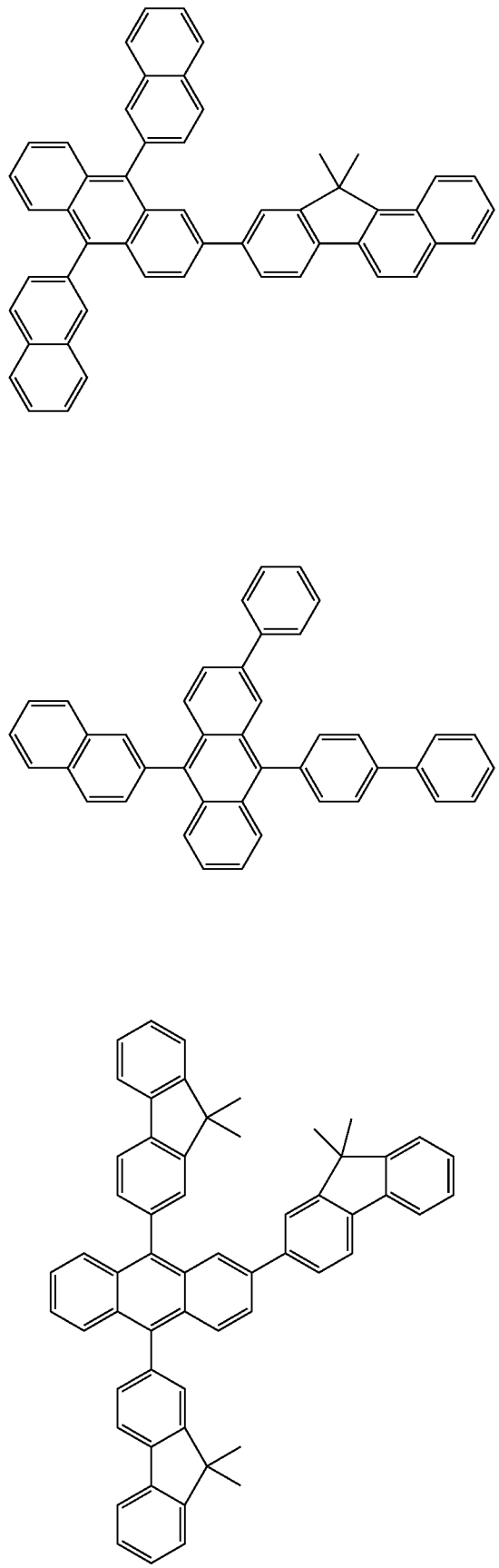

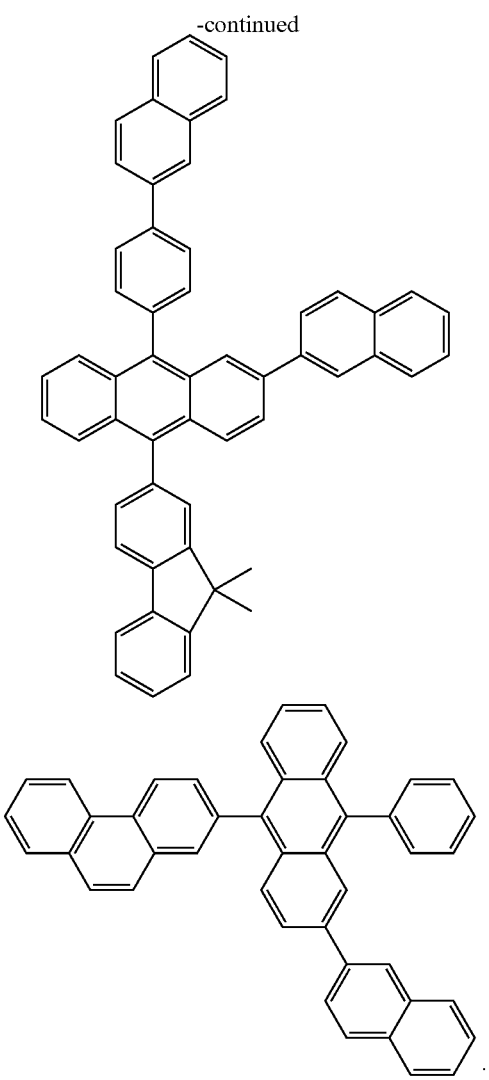

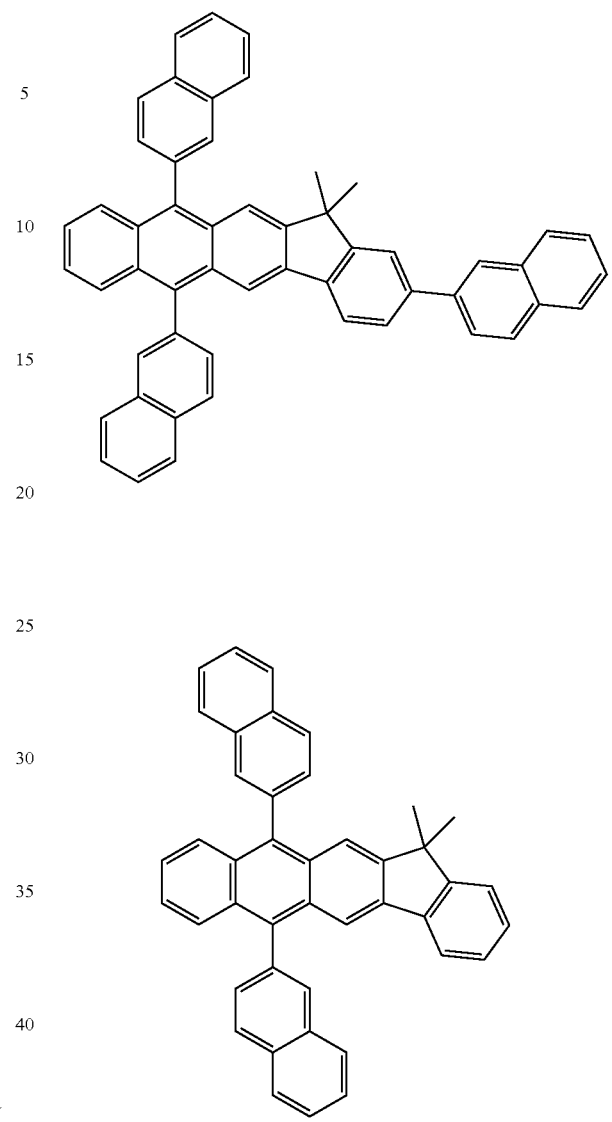

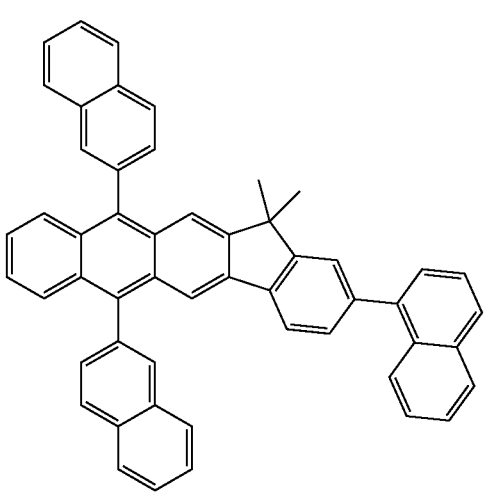

In some embodiments, an anthracene-based compound represented by Formula 401 below may be used as the host:

<Formula 401>

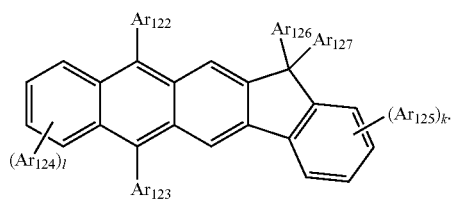

In Formula 401 above, $Ar_{122}$ to $Ar_{125}$ may be defined as described above in conjunction with $Ar_{113}$ of Formula 400.

In Formula 401 above, $Ar_{126}$ and $Ar_{127}$ may each independently be a $C_1$-$C_{10}$ alkyl group (e.g., a methyl group, an ethyl group, or a propyl group).

In Formula 401 above, k and l may each independently be an integer from 0 to 4, for example, 0, 1, or 2.

In some embodiments, the anthracene compound of Formula 401 above may be one of compounds represented by the Formulae below:

-continued
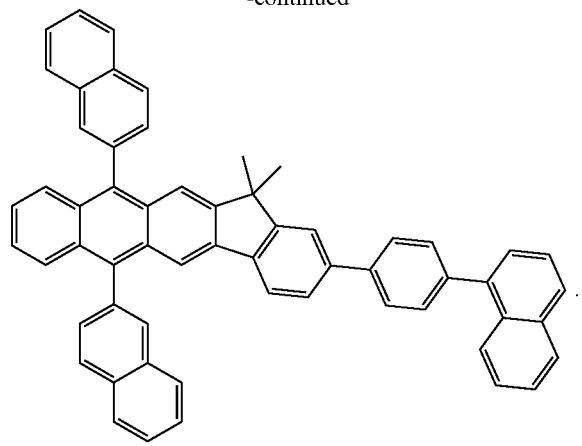
In an embodiment, the OLED is a full color OLED, and the EML may be patterned into a red EML, a green EML, and a blue EML.
Meanwhile, at least one layer of the red EML, the green EML, and the blue EML may include one of the dopants below (ppy=phenylpyridine).
Examples of the blue dopant are compounds represented by Formulae below:
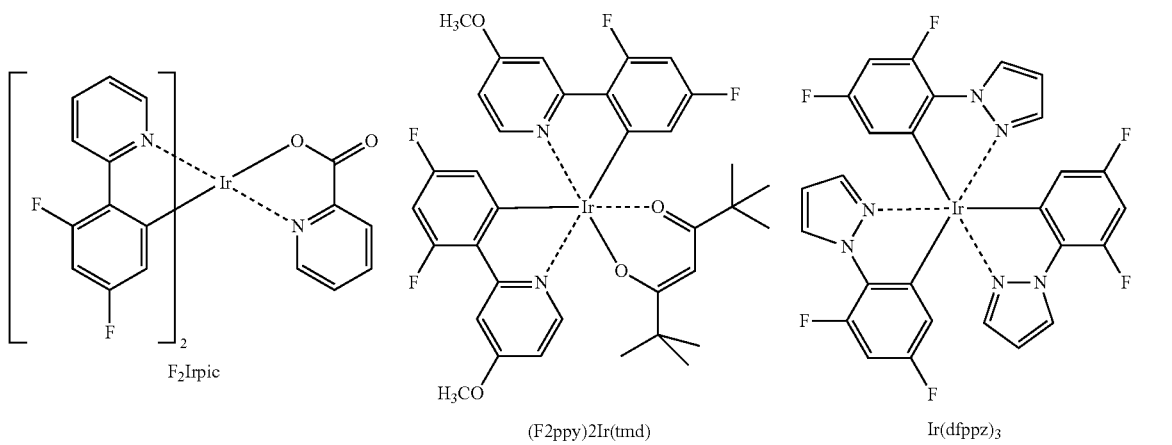
F₂Irpic    (F2ppy)2Ir(tmd)    Ir(dfppz)₃
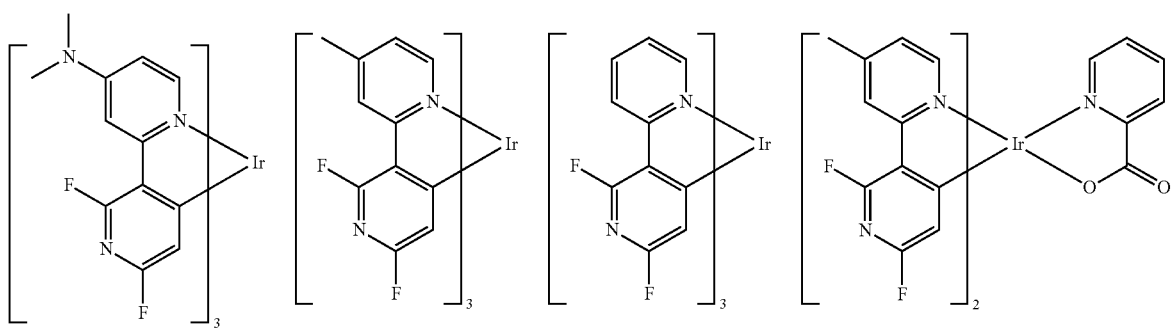
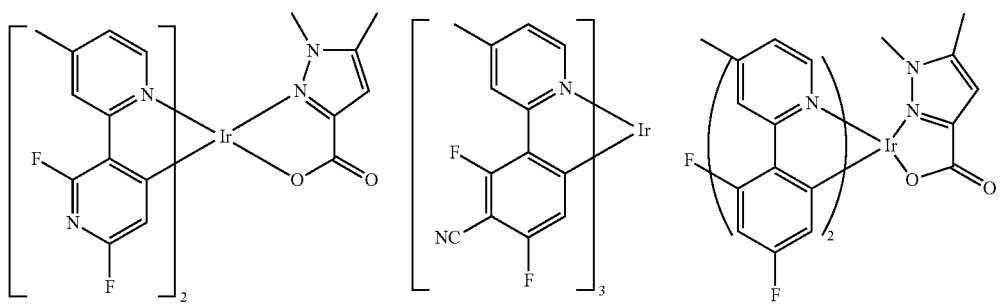

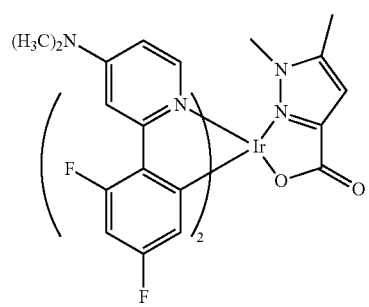
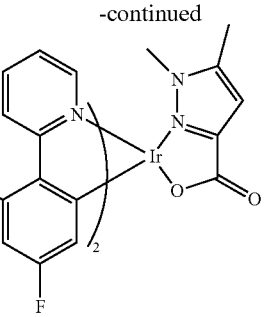
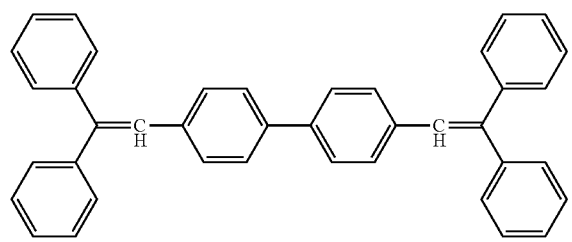
DPVBi
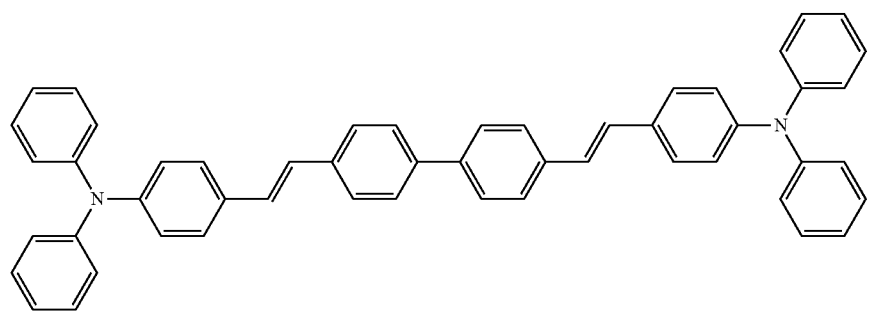
DPAVBi
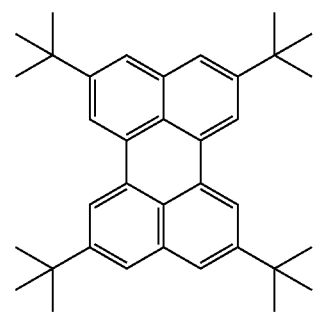
TBPe
Examples of the red dopant are compounds represented by Formulae below:
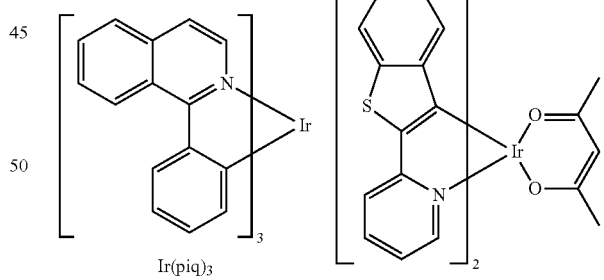
Ir(piq)₃
Btp₂Ir(acac)
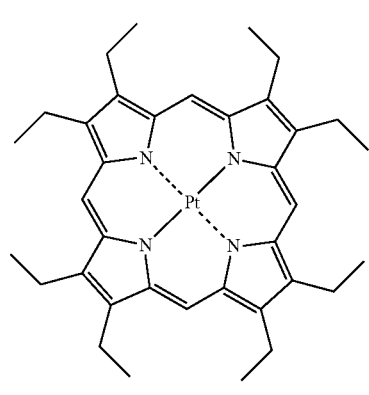
PtOEP
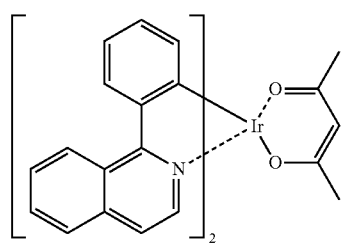

-continued
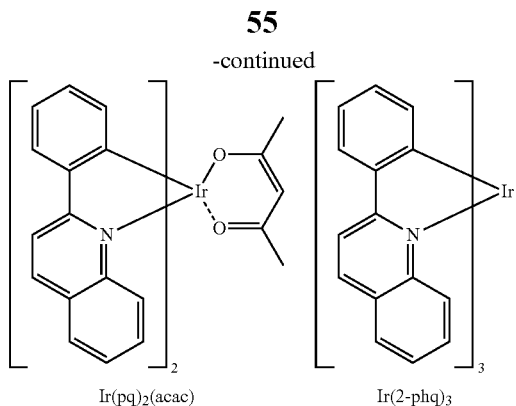
Ir(pq)₂(acac)　　Ir(2-phq)₃
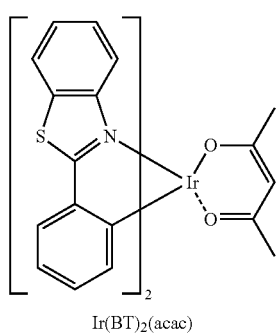
Ir(BT)₂(acac)
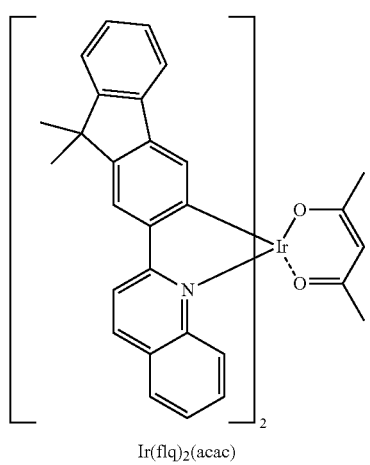
Ir(flq)₂(acac)
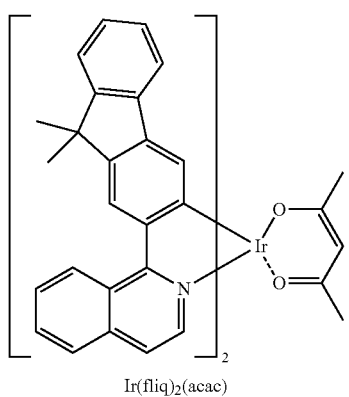
Ir(fliq)₂(acac)
-continued
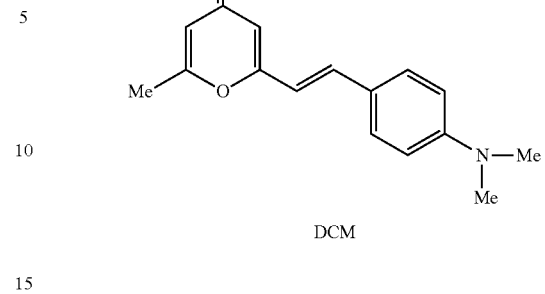
DCM
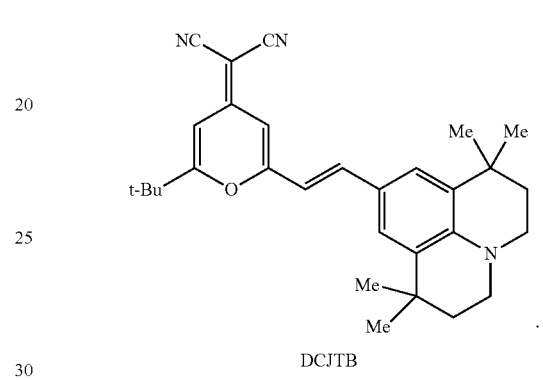
DCJTB
Examples of the green dopant are compounds represented by Formulae below:
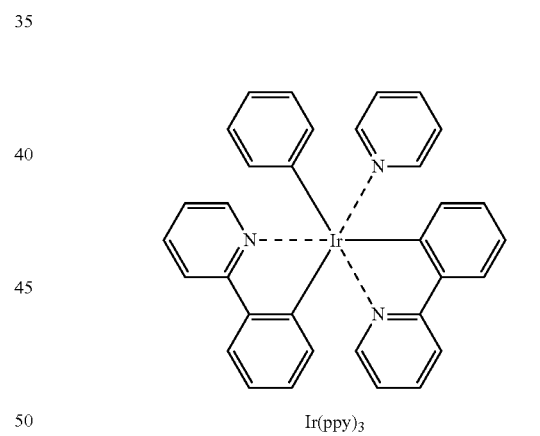
Ir(ppy)₃
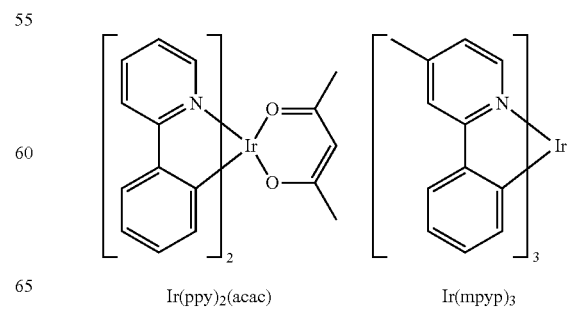
Ir(ppy)₂(acac)　　Ir(mpyp)₃

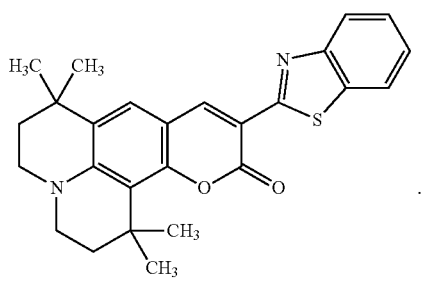
C545T
A dopant used in the EML may be a Pd-complex or a Pt-complex represented by Formulae below:
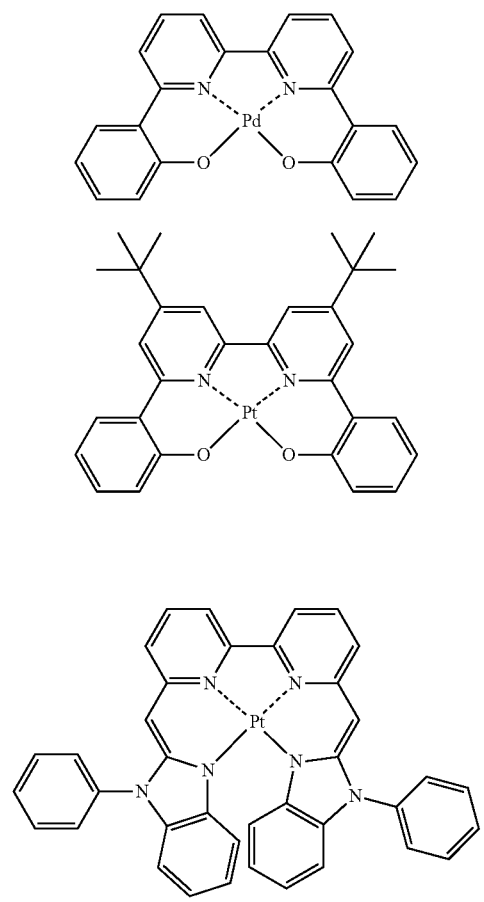
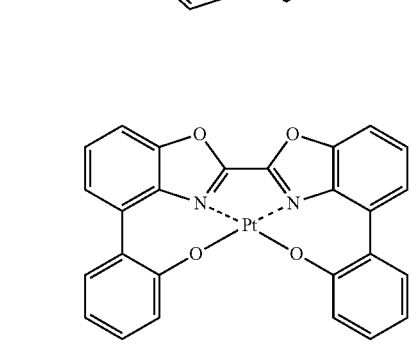
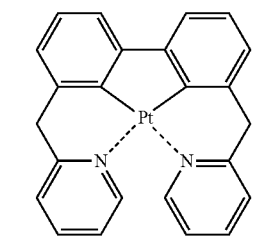
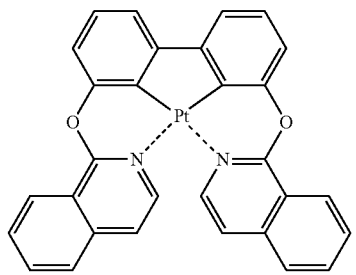
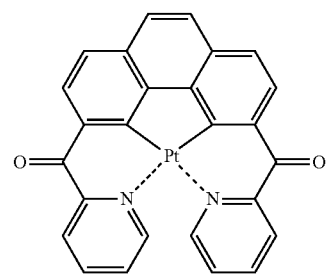
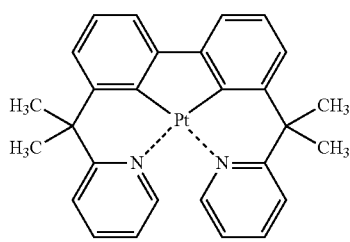
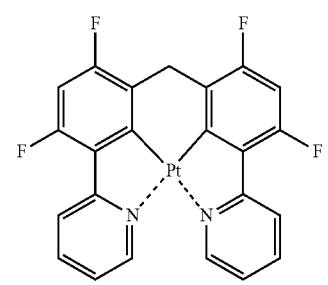
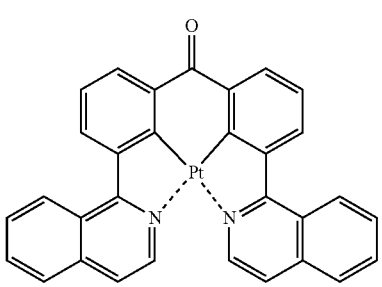

D11
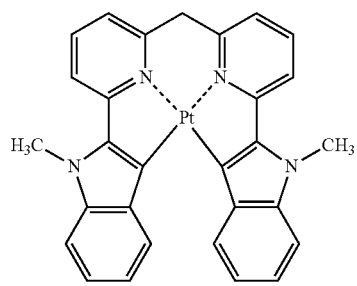
D12
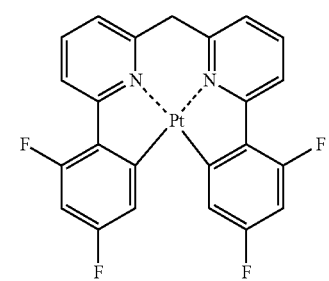
D13
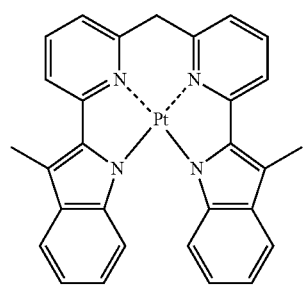
D14
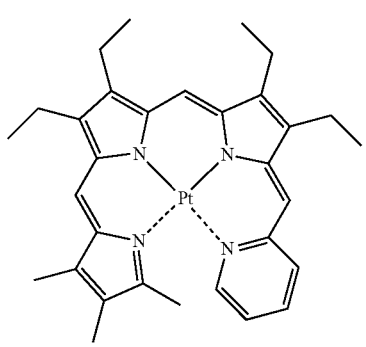
D15
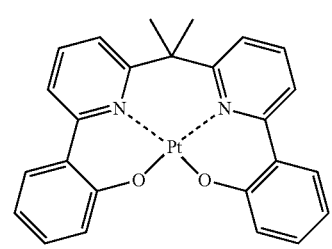
D16
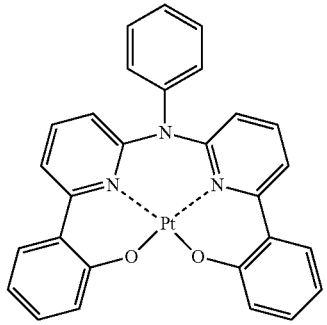
D17
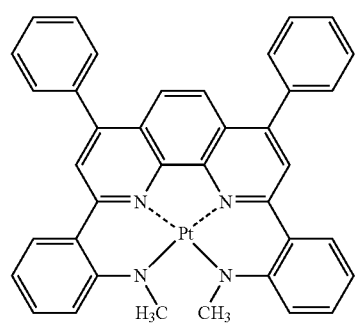
D18
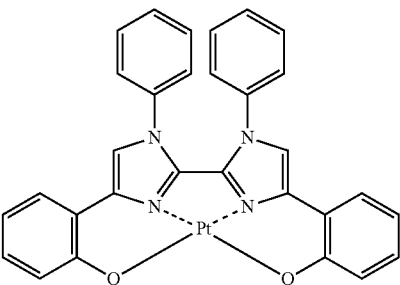
D19
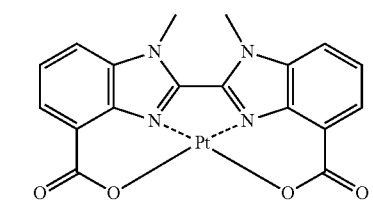
D20
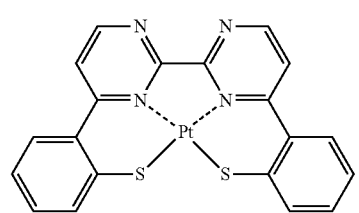

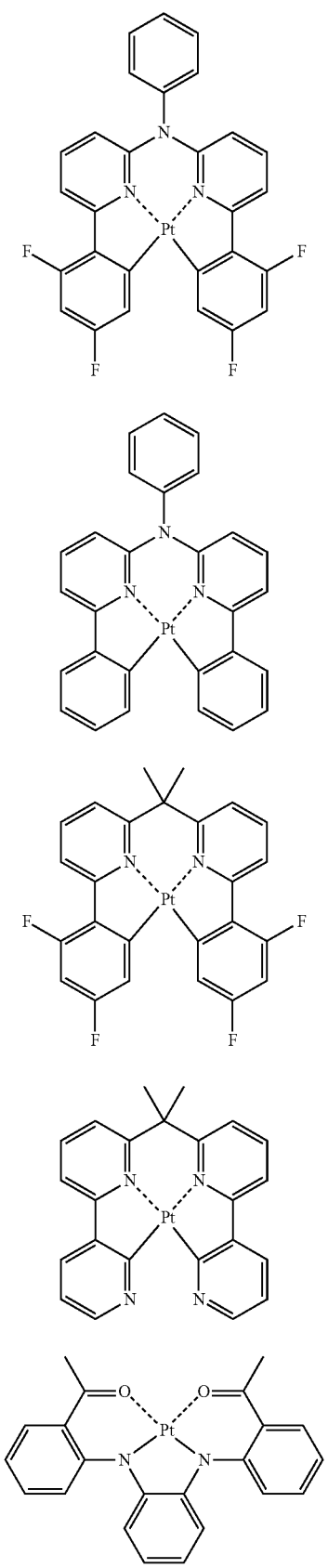
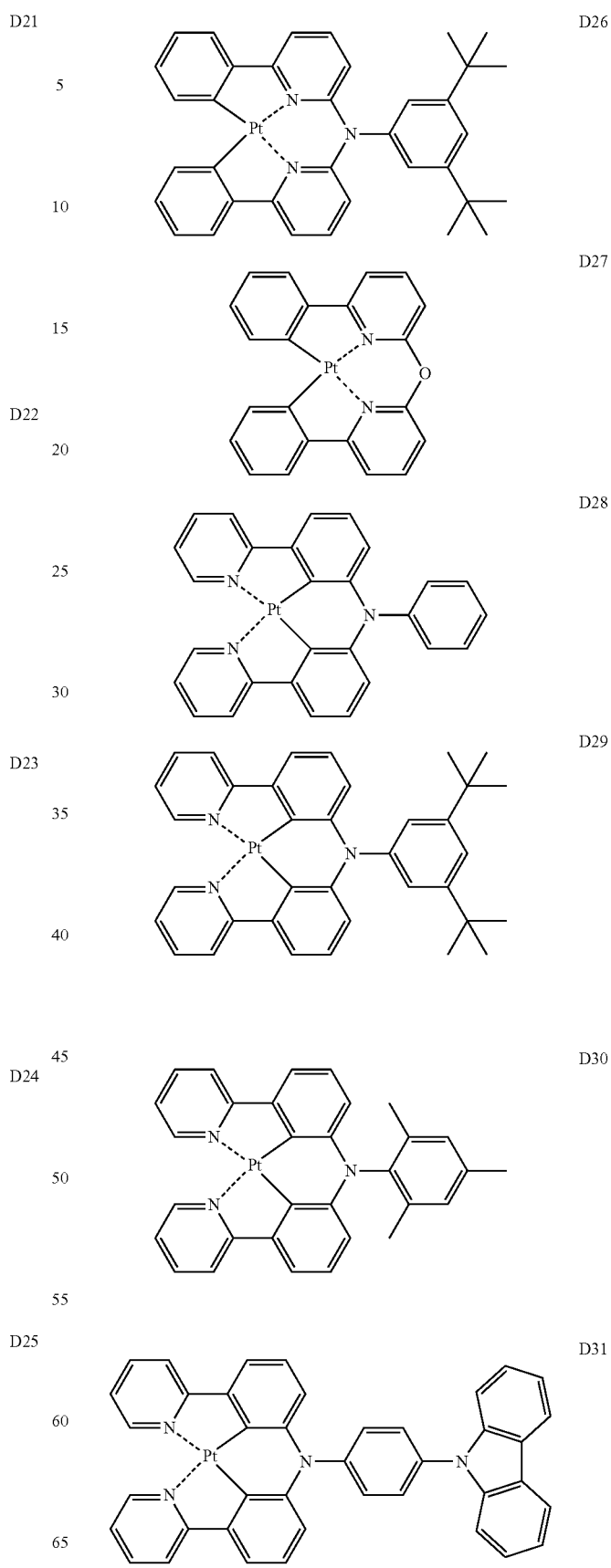

D32 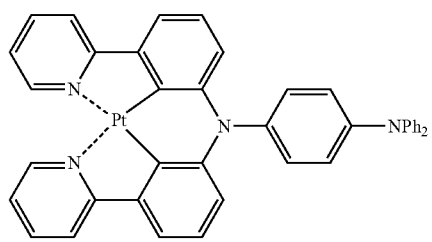
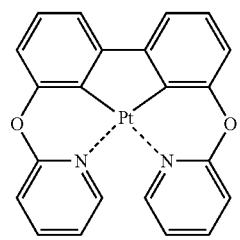
D34 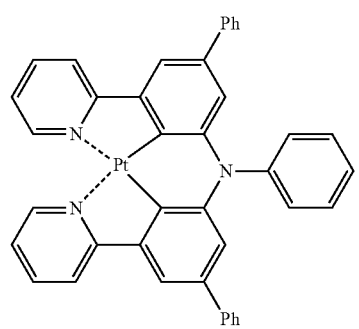
D35 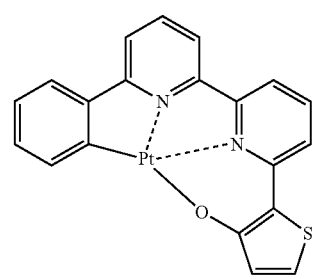
D36 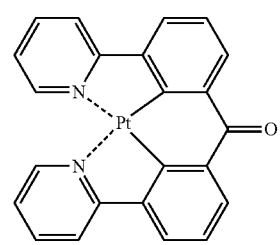
D37 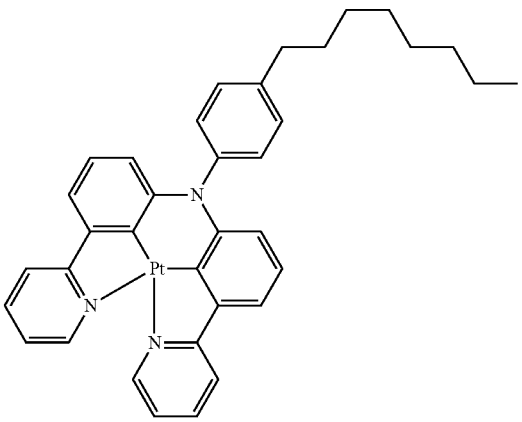
D38 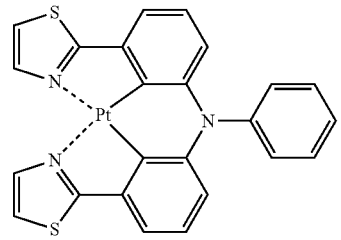
D39 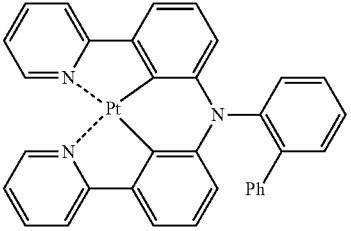
D40 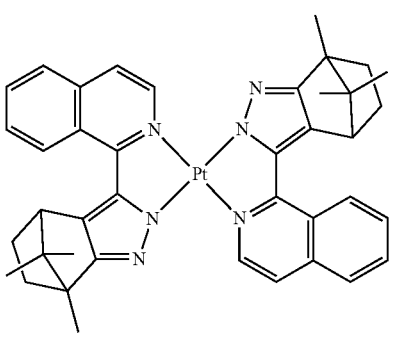
D41 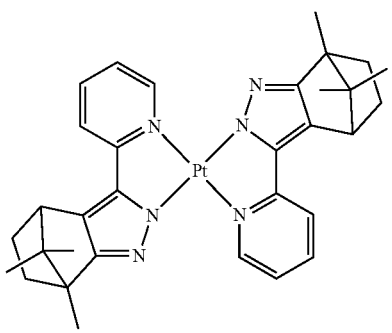

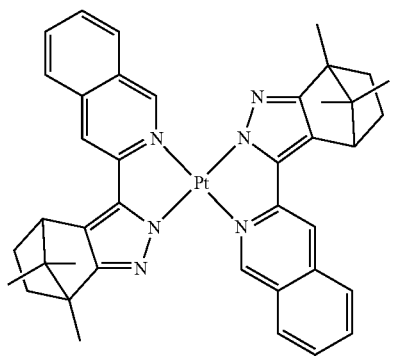
D42
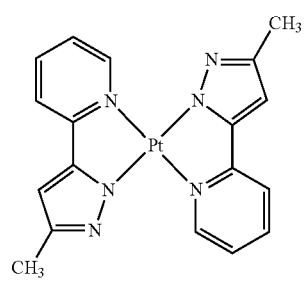
D43
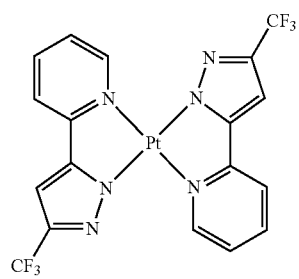
D44
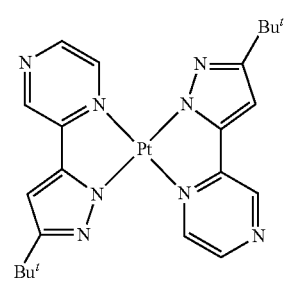
D45
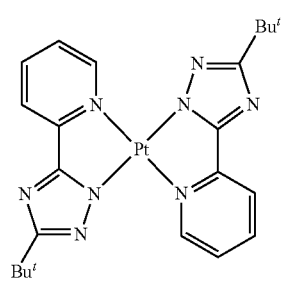
D46
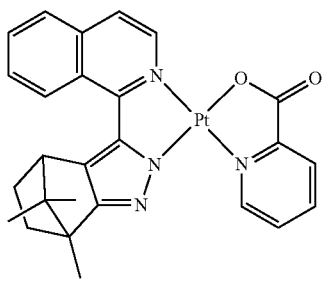
D47
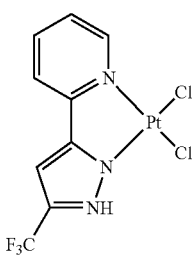
D48
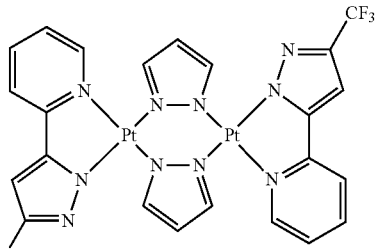
D49
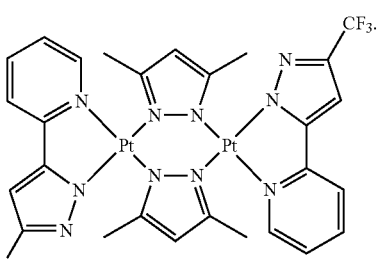
D50
Alternatively, a dopant used in the EML may be an Os-complex represented by Formulae below:
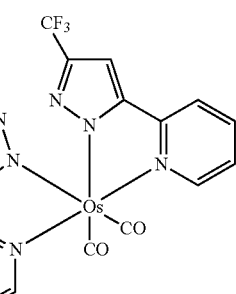
Os(fppz)₂(CO)₂

-continued

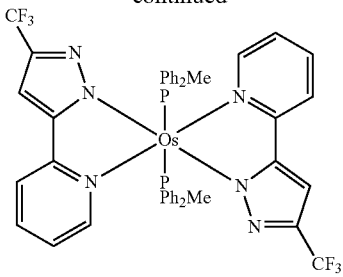

Os(fppz)₂(PPh₂Me)₂

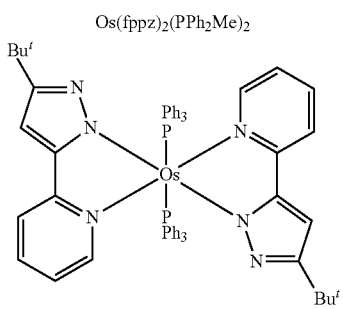

Os(bppz)₂(PPh₃)₂

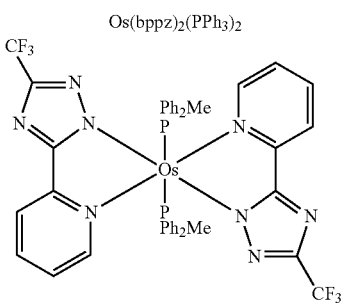

Os(fptz)₂(PPh₂Me)₂

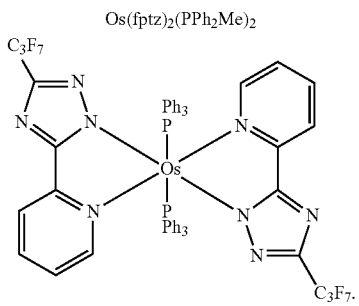

Os(hptz)₂(PPhMe₂)₂

In an embodiment, the EML includes a host and a dopant, and an amount of the dopant may be in a range of about 0.01 to about 15 parts by weight based on 100 parts by weight of the host.

A thickness of the EML may be in a range of about 100 Å to about 1,000 Å, for example, about 200 Å to about 600 Å. Maintaining the thickness of the EML within the above ranges may help provide the EML with satisfactory light-emitting capabilities without a substantial increase in driving voltage.

Then, an ETL may be formed on the EML by using various methods, such as vacuum deposition, spin coating, and casting. When the ETL is formed by using vacuum deposition or spin coating, the deposition and coating conditions may be similar to those for the formation of the HIL, although the deposition and coating conditions may vary depending on the compound that is used to form the ETL.

A material that may stably transport electrons that are injected from an electron injection electrode (i.e., a cathode) may be used as an ETL-forming material.

Examples of the ETL-forming materials include a quinoline derivative such as tris(8-quinolinorate)aluminum (Alq₃), TAZ, BAlq, beryllium bis(benzoquinolin-10-olate (Bebq₂), ADN, Compound 201, and Compound 202:

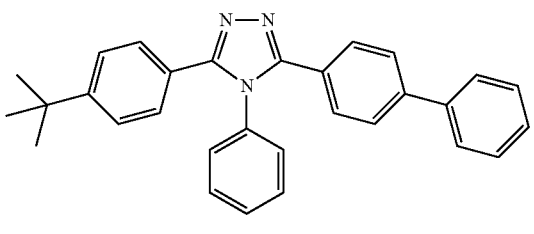

TAZ

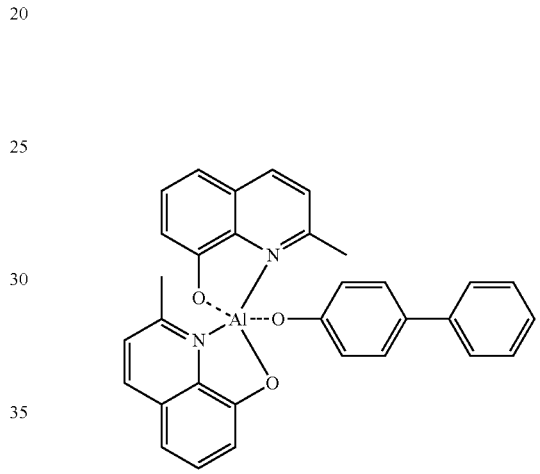

BAlq

<Compound 201>

<Compound 202>

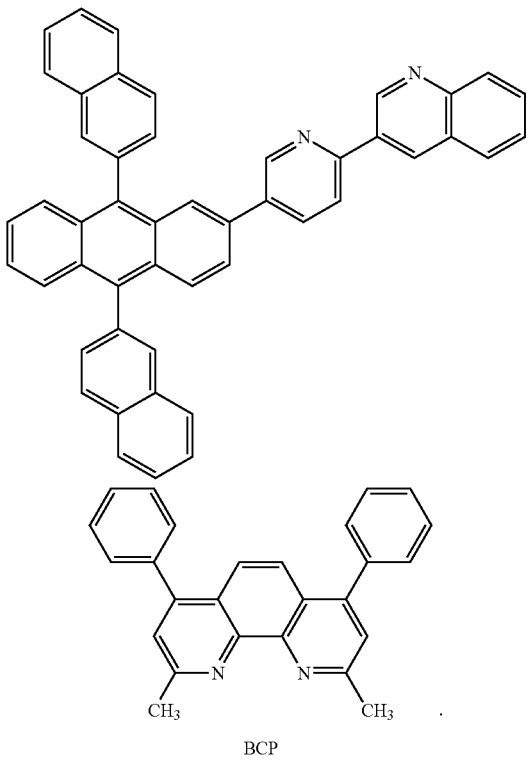

BCP

A thickness of the ETL may be in a range of about 100 Å to about 1,000 Å, for example, about 150 Å to about 500 Å. Maintaining the thickness of the ETL within the above ranges may help provide the ETL with satisfactory electron transporting capabilities without a substantial increase in driving voltage.

In some embodiments, the ETL may further include a metal-containing material, in addition to an organic compound for the ETL.

The metal-containing material may include a lithium (Li) complex. Examples of the Li complex include lithium quinolate (LiQ) and Compound 203 below:

<Compound 203>

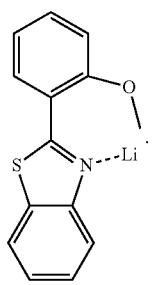

Then, an EIL, which facilitates injection of electrons from the cathode, may be formed on the ETL. Any suitable electron-injecting material may be used to form the EIL.

Examples of the EIL-forming materials include LiF, NaCl, CsF, Li$_2$O, and BaO. Deposition conditions of the EIL may be similar to those for the formation of the HIL, although the conditions may vary depending on the compound that is used to form the EIL.

A thickness of the EIL may be in a range of about 1 Å to about 100 Å, for example, about 3 Å to about 90 Å. Maintaining the thickness of the EIL within the above ranges may help provide the EIL with satisfactory electron injection capabilities without a substantial increase in driving voltage.

A second electrode is disposed on the organic layer. The second electrode may be a cathode, for example, an electron injection electrode, and materials that may have a low work function, such as a metal, an alloy, and an electro-conductive compound, and a mixture thereof may be used as the second electrode-forming material. The second electrode may be formed as a thin film type transmission electrode using lithium (Li), magnesium (Mg), aluminum (Al), aluminum-lithium (Al—Li), calcium (Ca), magnesium-indium (Mg—In), magnesium-silver (Mg—Ag). In some other embodiments, to manufacture a top-emission light-emitting diode, the transmission electrode may be formed of indium tin oxide (ITO) or indium zinc oxide (IZO).

The OLED has been described with reference to FIG. 1. Additional embodiments include omission of one or more of the layers illustrated in FIG. 1 (i.e., EIL, ETL, EML, HTL, and HIL), rearrangement of one or more of the layers illustrated in FIG. 1, and/or additional layers.

For example, when a phosphorescent dopant is used in the EML, a HBL may be formed between the ETL and the EML or between the E-functional layer and the EML by using vacuum deposition, spin coating, casting, or LB deposition, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Examples of hole-blocking materials include oxadiazole derivatives, triazole derivatives, and phenanthroline derivatives. For example, BCP below may be used to form the HBL.

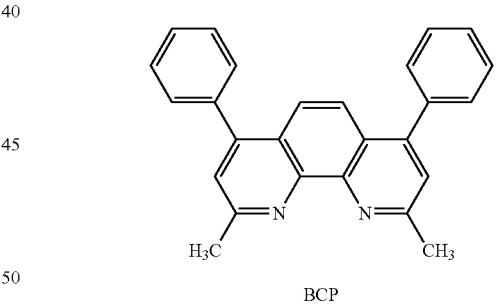

BCP

A thickness of the HBL may be in a range of about 20 Å to about 1,000 Å, for example, about 30 Å to about 300 Å. Maintaining the thickness of the HBL within the above ranges may help provide the HBL with satisfactory hole blocking capabilities without a substantial increase in driving voltage.

The OLED according to another embodiment may be provided in various types of flat panel display devices such as passive matrix OLED devices and active matrix OLED devices. For example, when the OLED is provided in an active matrix OLED, the first electrode acting as a pixel electrode on the substrate may be electrically connected to a source electrode or a drain electrode of a thin-film transistor (TFT). In addition, the OLED may be provided in a flat panel display device having double-sided screens.

Alternatively, the organic layer of the OLED according to another embodiment may be formed by using vacuum deposition using above-described compounds, or by using a wet process that coats the above-described compounds present in a liquid state.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 2

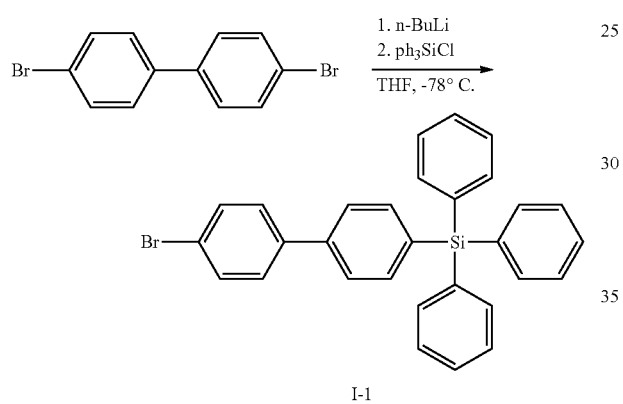

I-1

Synthesis of Intermediate I-1

3.12 g (10 mmol) of dibromobiphenyl was dissolved in 30 ml of THF, and 4 ml of n-butyl (2.5 M in hexane) was added thereto at a temperature of −78° C. After 1 hour, 2.95 g (10 mmol) of chlorotriphenylsilane was dissolved in 5 mL of THF at a temperature of −78° C., and then was slowly added to a mixture solution previously obtained. The mixture solution was stirred for 5 hours at room temperature, and water was added thereto. Then, the mixture solution was washed out three times with 30 ml of diethyl ether. The washed diethyl ether layer was dried by MgSO$_4$ and was vacuum-dried to obtain a reaction product. The reaction product was then separation-purified by silicagel column chromatography to obtain 2.9 g (Yield: 60%) of Intermediate I-1 as a white solid. The obtained compound was confirmed by liquid chromatography-mass spectrometry (LC-MS) (C$_{30}$H$_{23}$BrSi: M+ 491.0).

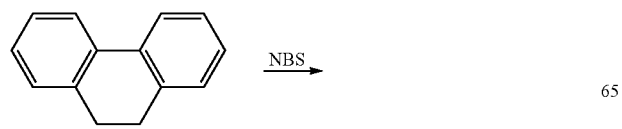

-continued

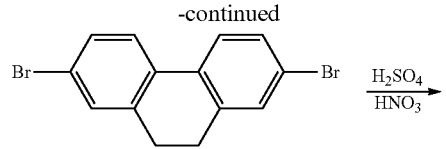

2-1

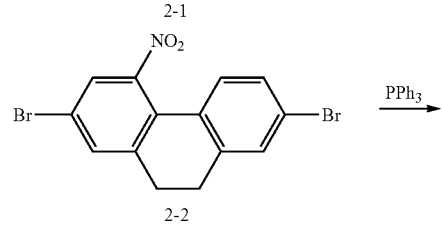

2-2

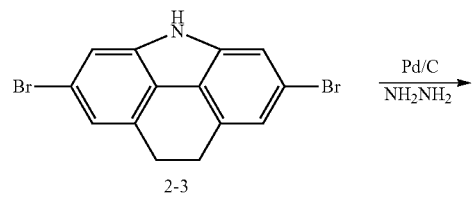

2-3

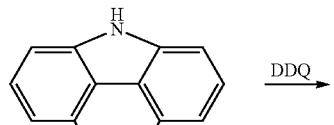

2-4

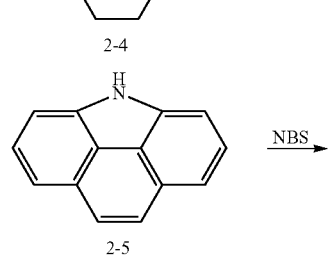

2-5

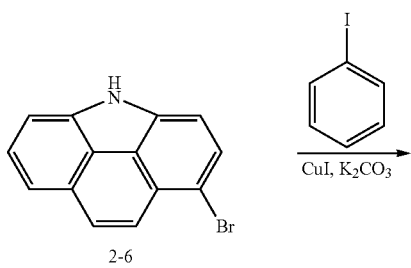

2-6

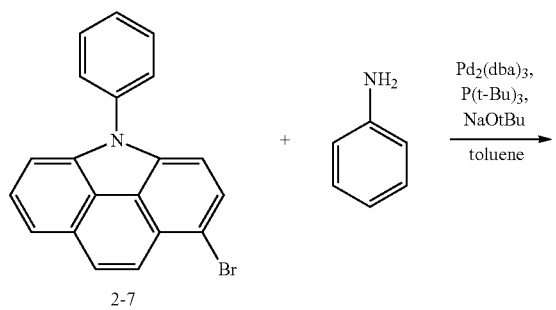

2-7

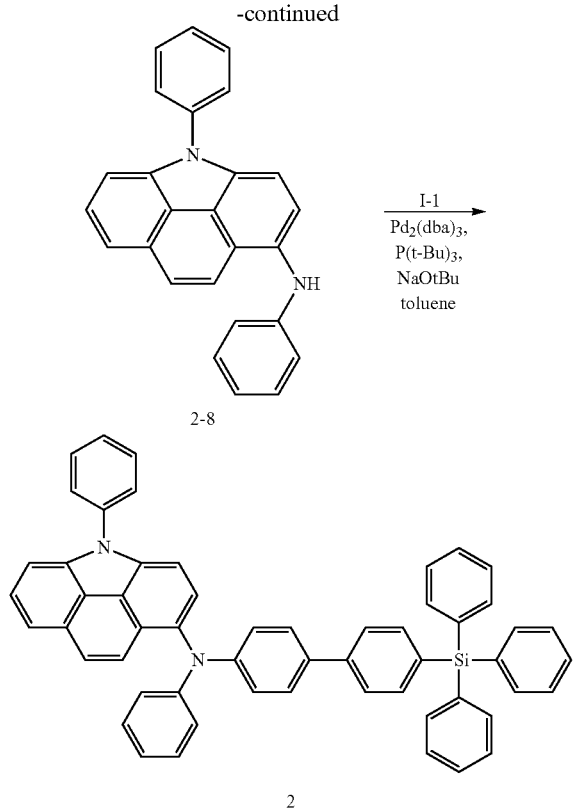

Synthesis Intermediate 2-1

10 g (55.4 mmol) of 9,10-dihydrophenanthrene, 21.8 g (121 mmol) of N-bromosuccinimide, and 0.5 g (2.7 mmol) of p-TsOH were dissolved in 30 ml of acetonitrile, and a mixture solution thereof was stirred for 12 hours at a temperature of 50° C. The mixture solution was cooled to room temperature, and then was stirred for 30 minutes to precipitate crystals. The crystals that were collected by a vacuum-filter were washed out with methanol to obtain 8.42 g (Yield: 45%) of Intermediate 2-1 as a gray crystal. The obtained compound was confirmed by LC-MS ($C_{14}H_{10}Br_2$: $M^+$ 336.9).

Synthesis Intermediate 2-2

5 g (15 mmol) of Intermediate 2-1 was completely dissolved in 50 ml of dichloromethane, and 1.7 g (30 mmol) of nitric acid was added thereto at room temperature. Then, 1.5 g (15 mmol) of sulfuric acid was slowly added to a mixture solution previously obtained, and the mixture solution was stirred for 6 hours at a temperature of 30° C. After completion of the reaction, the mixture solution was cooled to room temperature. Then, 50 ml of methanol was added thereto, and the mixture solution was stirred for 2 hours to precipitate crystals. The crystals that were collected by a vacuum-filter were washed out with methanol to obtain 5.2 g (Yield: 90%) of Intermediate 2-2. The obtained compound was confirmed by LC-MS ($C_{14}H_9Br_2NO_2$: $M^+$ 381.9).

Synthesis of Intermediate 2-3

4.6 g (12 mmol) of Intermediate 2-2 was dissolved in 30 ml of o-dichlorobenzene. After complete dissolution by heating a mixture solution previously obtained, 4.7 g (18 mmol) of triphenylphosphine was added thereto, and the mixture solution was stirred for 3 hours at a temperature of 180° C. The mixture solution was cooled to room temperature, and residues obtained by evaporation of the solvent were separation-purified by silicagel column chromatography to obtain 2.9 g (Yield: 70%) of Intermediate 2-3. The obtained compound was confirmed by LC-MS ($C_{14}H_9Br_2N$: $M^+$ 349.9).

Synthesis of Intermediate 2-4

10 g (28.5 mmol) of Intermediate 2-3 and 0.03 g (0.28 mmol) of Pd/C (10%) were dissolved in 100 ml of ethanol at room temperature. When the temperature rose to 50° C., 5.48 g (171 mmol) of hydrazine was added to a mixture solution previously obtained, and the mixture solution was stirred for 24 hours. After the mixture solution was cooled to room temperature, the mixture solution was washed out with acetone. Then, 100 ml of ice water was added thereto to obtain 3.63 g (Yield: 66%) of Intermediate 2-4 as a white crystal. The obtained compound was confirmed by LC-MS ($C_{14}H_{11}N$: M+ 194.1).

Synthesis of Intermediate 2-5

10 g (51.8 mmol) of Intermediate 2-4 was dissolved in 100 ml of toluene in an oxygen atmosphere, and 1.57 g (7.6 mol) of 2,3-dichloro-5,6,-dicyano-1,4-benzoquinone and 0.52 g (7.6 mmol) of $NaNO_2$ were added thereto. A mixture solution previously obtained was then stirred for 6 hours at a temperature of 110° C. The mixture solution was cooled to room temperature, and residues obtained by evaporation of the solvent were separation-purified by silicagel column chromatography to obtain 9 g (Yield: 91%) of Intermediate 2-5. The obtained compound was confirmed by LC-MS ($C_{14}H_9N$: M+ 192.1).

Synthesis of Intermediate 2-6

1.91 g (10 mmol) of Intermediate 2-5 was completely dissolved in 60 ml of carbon tetrachloride ($CCl_4$), and 1.78 g (10 mmol) of N-bromosuccinimide was added to a mixture solution previously obtained. The mixture solution was then stirred for 30 minutes at a temperature of 80° C. The mixture solution was cooled to room temperature, and was stirred for 30 minutes to precipitate crystals. The crystals that were collected by a vacuum-filter were washed out with methanol to obtain 1.22 g (Yield: 45%) of Intermediate 2-6 as a white crystal. The obtained compound was confirmed by LC-MS ($C_{14}H_8BrN$: $M^+$ 268.9).

Synthesis of Intermediate 2-7

2.7 g (10 mmol) of Intermediate 2-6, 2.5 g (12 mmol) of iodo benzene, 0.2 g (1 mmol) of 1,10-phenanthroline, 0.2 g (2 mmol) of CuI, and 4.1 g (30 mmol) of $K_2CO_3$ were dissolved in 30 ml of N,N-dimethylformamide (DMF), and a mixture solution thereof was stirred for 24 hours at a temperature of 80° C. The mixture solution was cooled to room temperature, and then was washed out three times with 30 ml of water and another three times with 40 ml of diethyl ester, to collect an organic layer. The organic layer was dried by magnesium sulfate, and residues obtained by evaporation of the solvent were separation-purified by silicagel column chromatography to obtain 3.11 g (Yield: 89%) of Intermediate 2-7. The obtained compound was confirmed by LC-MS ($C_{20}H_{12}BrN$: $M^+$ 346.0).

Synthesis of Intermediate 2-8

3.46 g (10 mmol) of Intermediate 2-7, 1.11 g (12 mmol) of aniline, 2.88 g (30 mmol) of t-BuONa, 183 mg (0.2 mmol) of $Pd_2(dba)_3$, and 40 mg (0.2 mmol) of $P(t-Bu)_3$ were dissolved in 40 ml of toluene, and a mixture solution thereof was stirred for 3 hours at a temperature of 90° C. After completion of the reaction, the mixture solution was cooled to room temperature, and distilled water was added thereto. Then, the mixture solution was extracted three times by 40 ml of diethyl ester to collect an organic layer. The organic layer was dried by magnesium sulfate, and residues obtained by evaporation of the solvent were separation-purified by silicagel column chromatography to obtain 2.37 g (Yield: 65%) of Intermediate 2-8. The obtained compound was confirmed by LC-MS ($C_{26}H_{18}N_2$: $M^+$ 359.2).

Synthesis of Compound 2

3.58 g (10 mmol) of Intermediate 2-8, 4.91 g (10 mmol) of Intermediate I-1, 2.88 g (30 mmol) of t-BuONa, 183 mg (0.2 mmol) of $Pd_2(dba)_3$, and 40 mg (0.2 mmol) of $P(t-Bu)_3$ were dissolved in 40 ml of toluene, and a mixture solution thereof was stirred for 3 hours at a temperature of 90° C. After completion of the reaction, the mixture solution was cooled to room temperature, and distilled water was added thereto. Then, the mixture solution was extracted three times by 40 ml of diethyl ester to collect an organic layer. The organic layer was dried by magnesium sulfate, and residues obtained by evaporation of the solvent were separation-purified by silicagel column chromatography to obtain 6.23 g (Yield: 81%) of Compound 2 as a white solid. The obtained compound was confirmed by MS/FAB and $^1H$ NMR ($C_{56}H_{40}N_2Si$: cal. 768.30, found 769.28, $^1H$ NMR ($CDCl_3$, 400 MHz) 7.77(d, 1H), 7.58(d, 6H), 7.53-7.22(m, 25H), 7.04(t, 2H), 6.84(d, 2H), 6.63(t, 1H), 6.50(d, 1H), 6.18(d, 2H)).

Synthesis Example 2

Synthesis of Compound 7

Synthesis of Intermediate I-2

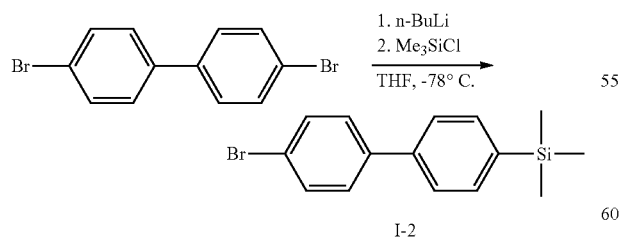

Intermediate I-2 was synthesized in the same manner as in Synthesis of Intermediate I-1, except that an intermediate of chlorotrimethylsilane instead of chlorotriphenylsilane was used. The obtained compound was confirmed by LC-MS ($C_{15}H_{17}BrSi$: $M^+$ 305.0).

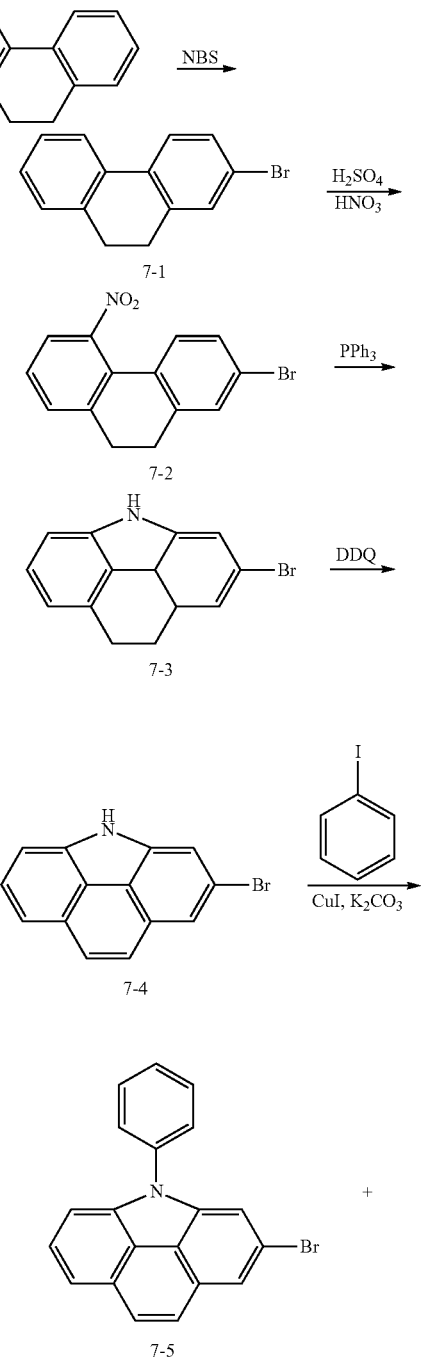

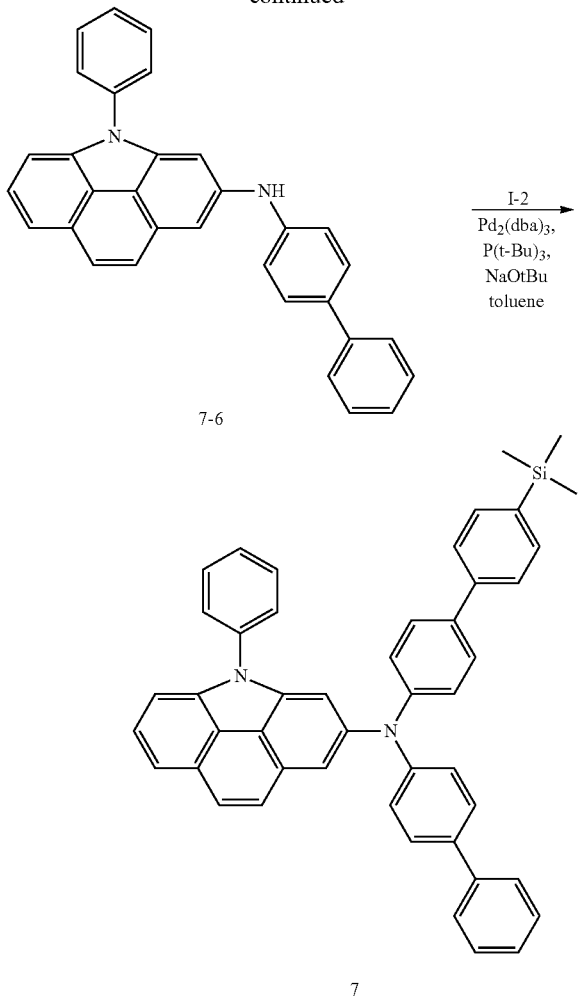

Synthesis of Intermediate 7-1

10 g (55.4 mmol) of 9,10-dihydrophenanthrene, 10.9 g (60.5 mmol) of N-bromosuccinimide, and 0.3 g (1.4 mmol) of p-TsOH were dissolved in 30 ml of acetonitrile, and a mixture solution thereof was stirred for 12 hours at a temperature of 50° C. The mixture solution was cooled to room temperature, and then was stirred for 30 minutes to precipitate crystals. The crystals that were collected by a vacuum-filter were washed out with methanol to obtain 6.4 g (Yield: 45%) of Intermediate 7-1 as a gray crystal. The obtained compound was confirmed by LC-MS ($C_{14}H_{11}Br$: $M^+$ 258.0).

Synthesis of Intermediate 7-2

3.9 g (15 mmol) of Intermediate 7-1 was completely dissolved in 50 ml of dichloromethane, and 1.7 g (30 mmol) of nitric acid was added thereto at room temperature. Then, 1.5 g (15 mmol) of sulfuric acid was slowly added to a mixture solution previously obtained, and the mixture solution was stirred for 6 hours at a temperature of 30° C. After completion of the reaction, the mixture solution was cooled to room temperature. Then, 50 ml of methanol was added thereto, and the mixture solution was stirred for 2 hours to precipitate crystals. The crystals that were collected by a vacuum-filter were washed out with methanol to obtain 4.1 g (Yield: 90%) of Intermediate 7-2. The obtained compound was confirmed by LC-MS ($C_{14}H_{10}BrNO_2$: $M^+$ 302.9).

Synthesis of Intermediate 7-3

3.6 g (12 mmol) of Intermediate 7-2 was dissolved in 30 ml of o-dichlorobenzene. After complete dissolution by heating a mixture solution previously obtained, 4.7 g (18 mmol) of triphenylphosphine was added thereto, and the mixture solution was stirred for 3 hours at a temperature of 180° C. The mixture solution was cooled to room temperature, and residues obtained by evaporation of the solvent were separation-purified by silicagel column chromatography to obtain 2.3 g (Yield: 70%) of Intermediate 7-3. The obtained compound was confirmed by LC-MS ($C_{14}H_{12}BrN$: $M^+$ 273.0).

Synthesis of Intermediate 7-4

2.7 g (10 mmol) of Intermediate 7-3 was dissolved in 100 ml of toluene in an oxygen atmosphere, and 0.6 g (0.3 mol) of 2,3-dichloro-5,6,-dicyano-1,4-benzoquinone and 0. 2 g (0.3 mmol) of $NaNO_2$ were added thereto. A mixture solution thereof was then stirred for 6 hours at a temperature of 110° C. The mixture solution was cooled to room temperature, and residues obtained by evaporation of the solvent were separation-purified by silicagel column chromatography to obtain 2.4 g (Yield: 90%) of Intermediate 7-4. The obtained compound was confirmed by LC-MS ($C_{14}H_8BrN$: $M^+$ 268.9).

Synthesis of Intermediate 7-5

2.6 g (10 mmol) of Intermediate 7-4, 2.5 g (12 mmol) of iodo benzene, 0.2 g (1 mmol) of 1,10-phenanthroline, 0.2 g (2 mmol) of CuI, and 4.1 g (30 mmol) of $K_2CO_3$ were dissolved in 30 ml of DMF, and a mixture solution thereof was stirred for 24 hours at a temperature of 80° C. The mixture solution was cooled to room temperature, and then was washed out three times with 30 ml of water and another three times with 40 ml of diethyl ester, to collect an organic layer. The organic layer was dried by magnesium sulfate, and residues obtained by evaporation of the solvent were separation-purified by silicagel column chromatography to obtain 3.1 g (Yield: 89%) of Intermediate 7-5. The obtained compound was confirmed by LC-MS ($C_{20}H_{12}BrN$: $M^+$ 345.0).

Synthesis of Intermediate 7-6

Intermediate 7-6 was synthesized in the same manner as in Synthesis of Intermediate 2-8, except that Intermediate 7-5 instead of Intermediate 2-7 was used and 4-aminobiphenyl instead of aniline was used. The obtained compound was confirmed by LC-MS ($C_{32}H_{22}N_2$: $M^+$ 434.1).

Synthesis of Compound 7

4.34 g (10 mmol) of Intermediate 7-6, 3.05 g (10 mmol) of Intermediate 1-2, 2.88 g (30 mmol) of t-BuONa, 183 mg (0.2 mmol) of $Pd_2(dba)_3$, and 40 mg (0.2 mmol) of $P(t-Bu)_3$ were dissolved in 40 ml of toluene, and a mixture solution thereof was stirred for 3 hours at a temperature of 90° C. After completion of the reaction, the mixture solution was cooled to room temperature, and distilled water was added thereto. Then, the mixture solution was extracted three times by 40 ml of diethyl ester to collect an organic layer. The organic layer was dried by magnesium sulfate, and residues obtained by evaporation of the solvent were separation-purified by silicagel column chromatography to obtain 4.94 g (Yield: 75%) of Compound 7. The obtained compound was confirmed by MS/FAB and $^1H$ NMR ($C_{47}H_{38}N_2Si$ cal. 658.28, found 659.23, $^1H$ NMR ($CDCl_3$, 400 MHz) 7.77(d, 1H), 7.65-7.34(m, 23H), 6.81-6.73(m, 5H), 0.35(s, 9H)).

Other additional compounds were synthesized in the same manner as in the above-described synthesis pathways using appropriate intermediates. Results of synthesized compounds confirmed by $^1H$ NMR and MS/FAB are shown in Table 1 below.

TABLE 1

| Compound | $^1$H NMR (CDCl$_3$, 400 MHz) | MS/FAB Found | Calc. |
| --- | --- | --- | --- |
| 2 | 7.77 (d, 1H), 7.58 (d, 6H), 7.53-7.22 (m, 25H), 7.04 (t, 2H), 6.84 (d, 2H), 6.63 (t, 1H), 6.50 (d, 1H), 6.18 (d, 2H) | 769.32 | 768.30 |
| 7 | 7.77 (d, 1H), 7.65-7.34 (m, 23H), 6.81-6.73 (m, 5H), 0.35 (s, 9H) | 659.29 | 658.28 |
| 12 | 7.78 (d, 1H), 7.59 (d, 6H), 7.53-7.22 (m, 25H), 6.87 (t, 2H), 6.70 (d, 1H), 6.55 (d, 2H), 6.49-6.45 (m, 2H) | 787.30 | 786.29 |
| 30 | 8.03 (d, 1H), 7.86 (d, 1H), 7.77 (d, 1H), 7.58 (d, 6H), 7.51-7.07 (m, 28H), 6.78 (d, 1H), 6.68 (d, 1H), 6.38 (d, 2H) | 837.27 | 836.30 |
| 33 | 7.77 (d, 1H), 7.66-7.61 (m, 8H), 7.57-7.46 (m, 6H), 7.42-7.29 (m, 10H), 7.26-7.22 (m, 4H), 7.11-7.06 (m, 3H), 6.95 (s, 1H), 6.75 (d, 1H), 6.65 (t, 1H), 6.49 (s, 1H), 6.33 (d, 2H), 1.32 (s, 6H) | 809.30 | 808.33 |
| 42 | 8.15 (m, 1H), 7.88 (m, 1H), 7.78-7.76 (m, 2H), 7.70-7.64 (m, 7H), 7.59-7.47 (m, 14H), 7.41-7.19 (m, 18H), 6.89 (d, 1H), 6.59 (d, 1H) | 908.32 | 907.34 |
| 47 | 7.77 (d, 1H), 7.65-7.22 (m, 34H), 6.85 (d, 2H), 6.77-6.73 (m, 3H) | 769.33 | 768.30 |
| 56 | 8.09 (d, 1H), 7.78 (d, 1H), 7.66-7.61 (m, 8H), 7.56-7.29 (m, 25H), 7.26-7.22 (m, 3H), 7.00 (d, 1H), 6.77 (d, 1H), 6.50 (d, 2H) | 819.29 | 818.31 |

Example 1

An anode was prepared by cutting a Corning 15 Ω/cm$^2$ (1200 Å) ITO glass substrate to a size of 50 mm×50 mm×0.7 mm, sonicated in isopropyl alcohol for about 5 minutes and in pure water for about 5 minutes, and then cleaned by irradiation of ultraviolet rays for about 30 minutes, and exposed to ozone. The resulting glass substrate was loaded into a vacuum deposition device.

4,4',4"-Tris(N-(2-naphthyl)-N-phenyl-amino)-triphenylamine (hereinafter, referred to as 2-TNATA), which is a compound for an HIL, was vacuum-deposited on the anode to a thickness of about 600 Å to form an HIL, and Compound 2 of Formula 1 above as a hole transporting compound was vacuum-deposited on the HIL to a thickness of about 300 Å to form an HTL.

9,10-di-naphthalene-2-yl-anthracene (hereinafter, referred to as DNA) as a blue fluorescent host, and 4,4'-bis[2-(4-(N,N-diphenylamino)phenyl)vinyl]biphenyl (hereinafter, referred to as DPAVBi) as a blue fluorescent dopant, were co-deposited at a weight ratio of about 98:2 on the HTL to form an EML having a thickness of 300 Å.

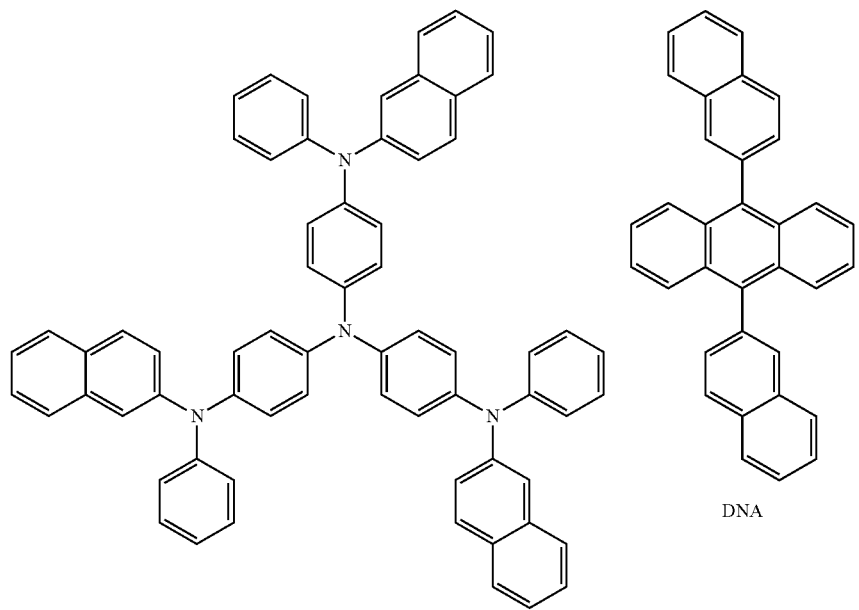

2-THATA

DNA

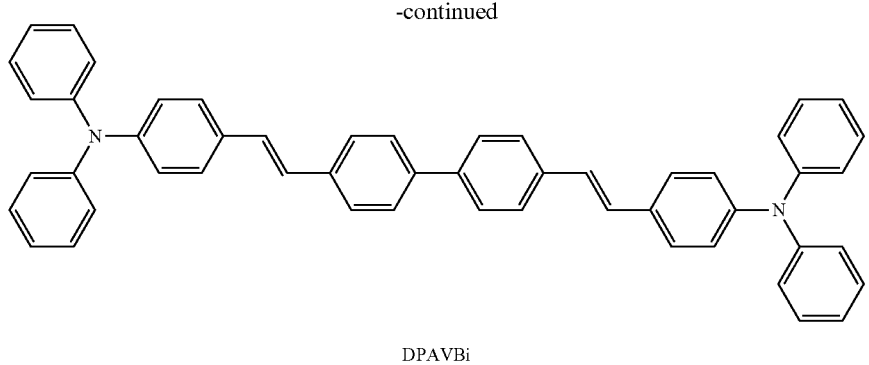

DPAVBi

Next, Alq$_3$ was deposited on the EML to form an ETL to a thickness of 300 Å, and then LiF, which is a halogenated alkali metal, was deposited on the ETL to form an EIL to a thickness of 10 Å. Then, Al was vacuum-deposited on the EIL to a thickness of 3,000 Å to form a LiF/Al cathode, thereby manufacturing an OLED.

Example 2

An OLED was manufactured in the same manner as in Example 1, except that Compound 7 instead of Compound 2 was used to form the HTL.

Example 3

An OLED was manufactured in the same manner as in Example 1, except that Compound 12 instead of Compound 2 was used to form the HTL.

Example 4

An OLED was manufactured in the same manner as in Example 1, except that Compound 30 instead of Compound 2 was used to form the HTL.

Example 5

An OLED was manufactured in the same manner as in Example 1, except that Compound 33 instead of Compound 2 was used to form the HTL.

Example 6

An OLED was manufactured in the same manner as in Example 1, except that Compound 42 instead of Compound 2 was used to form the HTL.

Example 7

An OLED was manufactured in the same manner as in Example 1, except that Compound 47 instead of Compound 2 was used to form the HTL.

Example 8

An OLED was manufactured in the same manner as in Example 1, except that Compound 56 instead of Compound 2 was used to form the HTL.

Comparative Example 1

An OLED was manufactured in the same manner as in Example 1, except that 4,4'-bis[N-(1-naphthyl)-N-phenylamino]biphenyl (hereinafter, referred to as NPB), which is a hole transporting compound, instead of Compound 2 was used to form the HTL.

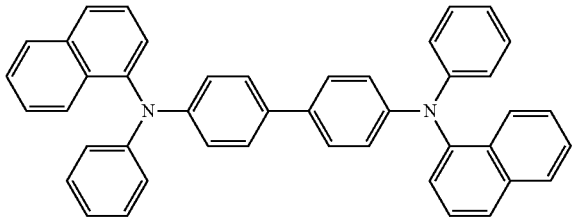

NPB

Examples 1-8, using compounds of Formula 1 above as hole transporting materials, hd improved driving voltage and excellent I-V-L characteristics with enhanced efficiency compared to NPB. In addition, Examples 1-8 had long lifespan. Representative characteristics and results are summarized in Table 2 below.

TABLE 2

|  | Hole transporting material | Driving voltage (V) | Current density (mA/cm$^2$) | Luminance (cd/m$^2$) | Efficiency (cd/A) | Luminous color | Half lifespan (hr @100 mA/cm$^2$) |
| --- | --- | --- | --- | --- | --- | --- | --- |
| Example 1 | Compound 2 | 5.52 | 50 | 2,605 | 5.21 | Blue | 228 |
| Example 2 | Compound 7 | 5.45 | 50 | 2,660 | 5.32 | Blue | 215 |
| Example 3 | Compound 12 | 5.62 | 50 | 2,770 | 5.54 | Blue | 232 |
| Example 4 | Compound 30 | 5.43 | 50 | 2,715 | 5.43 | Blue | 275 |
| Example 5 | Compound 33 | 5.34 | 50 | 2,560 | 5.12 | Blue | 255 |
| Example 6 | Compound 42 | 5.65 | 50 | 2,615 | 5.23 | Blue | 235 |
| Example 7 | Compound 47 | 5.41 | 50 | 2,665 | 5.33 | Blue | 221 |
| Example 8 | Compound 56 | 5.59 | 50 | 2,710 | 5.42 | Blue | 219 |

TABLE 2-continued

| | Hole transporting material | Driving voltage (V) | Current density (mA/cm$^2$) | Luminance (cd/m$^2$) | Efficiency (cd/A) | Luminous color | Half lifespan (hr @100 mA/cm$^2$) |
|---|---|---|---|---|---|---|---|
| Comparative Example 1 | NPB | 7.35 | 50 | 2,065 | 4.13 | Blue | 145 |

By way of summation and review, an OLED device may have a structure including a substrate, an anode formed on the substrate, and a hole transport layer (HTL), an emission layer (EML), an electron transport layer (ETL), and a cathode that are sequentially stacked on the anode. The HTL, the EML, and the ETL are organic thin films formed using organic compounds.

When a voltage is applied between the anode and the cathode, holes injected from the anode pass via the hole transport layer and migrate toward the emission layer, and electrons injected from the cathode pass via the electron transport layer and migrate toward the emission layer. The holes and the electrons are recombined with each other in the emission layer to generate excitons. Then, the excitons are transitioned from an excited state to a ground state, thereby generating light.

According to an embodiment, provided is a material that may have excellent electrical stability, high charge-transport ability or light-emitting ability, high glass transition temperature, and the ability to prevent crystallization, for example, in comparison with organic monomolecular materials.

One or more embodiments include a material that may be suitable for fluorescent and phosphorescent devices of various colors including red, green, blue, and white. One or more embodiments include an amine-based compound and an OLED including the same.

An anthracene derivative may be included in an organic light-emitting layer of an OLED. For example, the OLED may include a dimer or trimer of phenylanthracene. An OLED including two or three anthracene derivatives that are conjugated to each other may have decreased energy gap and lower color purity of blue emission. The anthracene derivative may be difficult to purify, may become oxidized, and may become contaminated with impurities. An OLED including an anthracene compound having naphthalene substituted at a 1,9-position, or a diphenylanthracene compound having an aryl group substituted at an m-position of a phenyl group, may have low emission efficiency. An OLED including a mono-anthracene derivative having substituted naphthalene may have low emission efficiency of about 1 cd/A.

An OLED including a compound having a phenylanthracene structure, with an aryl group substituted at an m-position of phenylanthracene, may not provide satisfactory emission characteristics, and may have low emission efficiency of about 2 cd/A, although it may have excellent thermal resistance. An OLED including one or more carbazole-based derivatives and/or arylamine-based derivatives, for example, as a hole-injecting material, may have high driving voltage, low efficiency, and short lifespan.

According to an embodiment, the heterocyclic compound of Formula 1 may have excellent hole transport or hole injection capabilities, and may be suitable as a hole-injecting or hole-transporting material for fluorescent and phosphorescent devices of various colors including red, green, blue, and white.

As described above, according to the one or more of the above embodiments, an organic light-emitting diode including a compound represented by Formula 1 above may have characteristics of excellent hole injection or hole transport capability and may be suitable for fluorescent and phosphorescent devices of various colors including red, green, blue, and white. When such a compound is used, an organic light-emitting diode having high efficiency, low brightness, and long lifespan may be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by Formula 1:

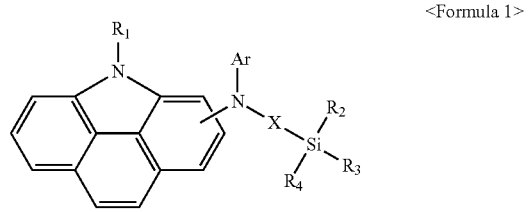

<Formula 1> wherein $R_1$ to $R_4$ are each independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_2$-$C_{60}$ heteroaryl group, a substituted or unsubstituted $C_6$-$C_{60}$ aryloxy group, or a substituted or unsubstituted $C_6$-$C_{60}$ arylthio group;

Ar is a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; and X is a single bond, a substituted or unsubstituted $C_6$-$C_{60}$ arylene group, a substituted or unsubstituted $C_2$-$C_{60}$ heteroarylene group, or a substituted or unsubstituted $C_6$-$C_{60}$ condensed polycyclic group, or a divalent linking group in which at least two of the substituted or unsubstituted $C_6$-$C_{60}$ arylene group, the substituted or unsubstituted $C_2$-$C_{60}$ heteroarylene group, and the substituted or unsubstituted $C_6$-$C_{60}$ condensed polycyclic group are connected.

2. The heterocyclic compound as claimed in claim 1, wherein $R_1$ of Formula 1 is represented by Formula 2a or Formula 2b:

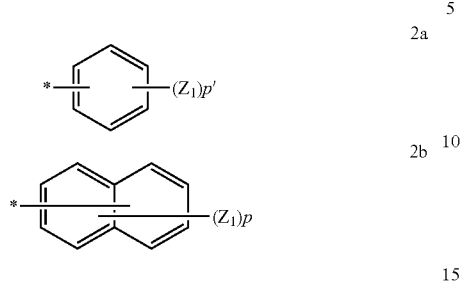

wherein $Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group, wherein $Z_1$ is different from or identical to each other when there is a plurality of $Z_1$s;

p' is an integer of 1 to 5;

p is an integer from 1 to 7; and

* indicates a binding site.

3. The heterocyclic compound as claimed in claim 1, wherein Ar of Formula 1 is represented by one of Formulae 3a to 3c:

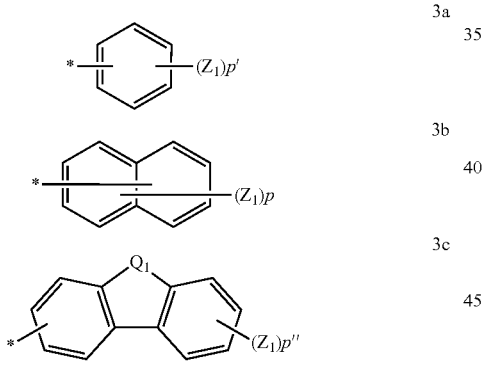

wherein $Q_1$ is —$CR_{11}R_{12}$—, —$NR_{21}$—, or —O—;

$R_{11}$, $R_{12}$, $R_{21}$, and $Z_1$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group, wherein $Z_1$ is different from or identical to each other when there is a plurality of $Z_1$s;

p' is an integer of 1 to 5;

p" is an integer of 1 to 4;

p is an integer from 1 to 7; and

* indicates a binding site.

4. The heterocyclic compound as claimed in claim 1, wherein X of Formula 1 is represented by one of Formulae 4a to 4c:

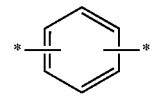

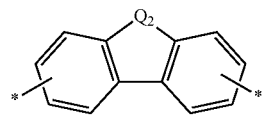

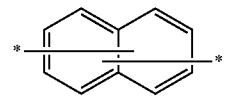

wherein $Q_2$ is —$CR_{11}R_{12}$—, or —$NR_{21}$—;

$R_{11}$, $R_{12}$, and $R_{21}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group; and

* indicates a binding site.

5. The heterocyclic compound as claimed in claim 1, wherein $R_2$, $R_3$, and $R_4$ of Formula 1 are each independently a $C_1$-$C_{20}$ alkyl group or represented by Formula 5a:

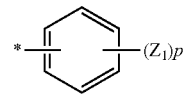

wherein $Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxyl group, or a carboxyl group, wherein $Z_1$ is different from or identical to each other when there is a plurality of $Z_1$s;

p is an integer from 1 to 5; and

* indicates a binding site.

6. The heterocyclic compound as claimed in claim 1, wherein the heterocyclic compound of Formula 1 is one of the compounds:

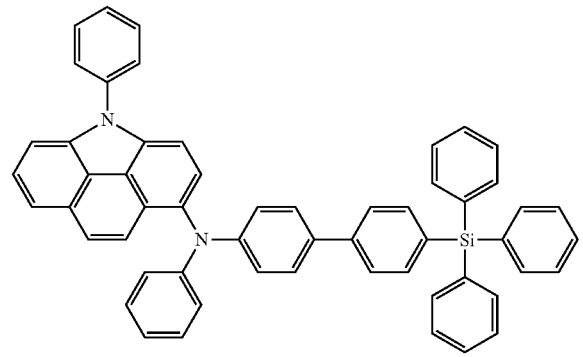
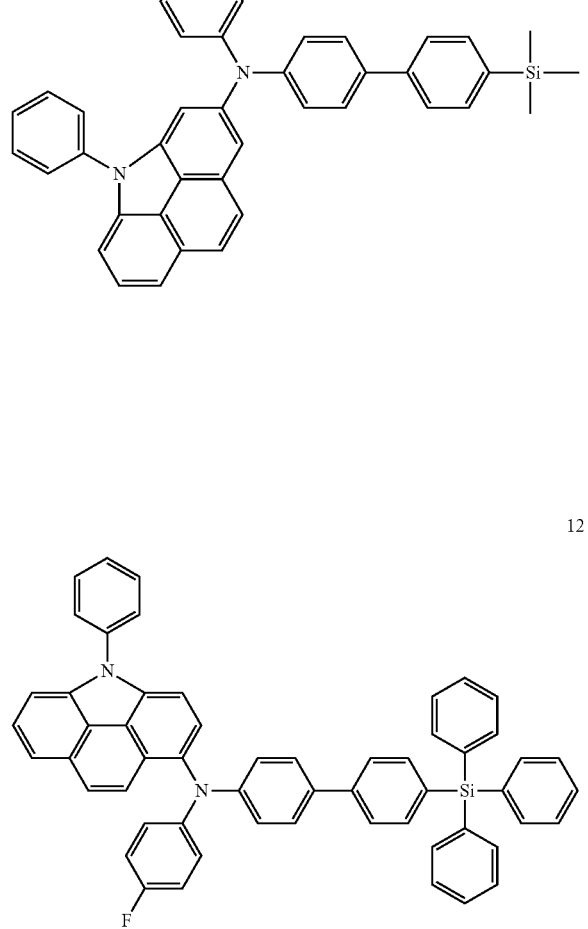
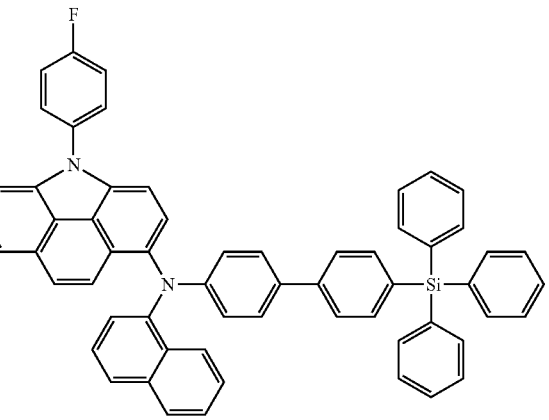
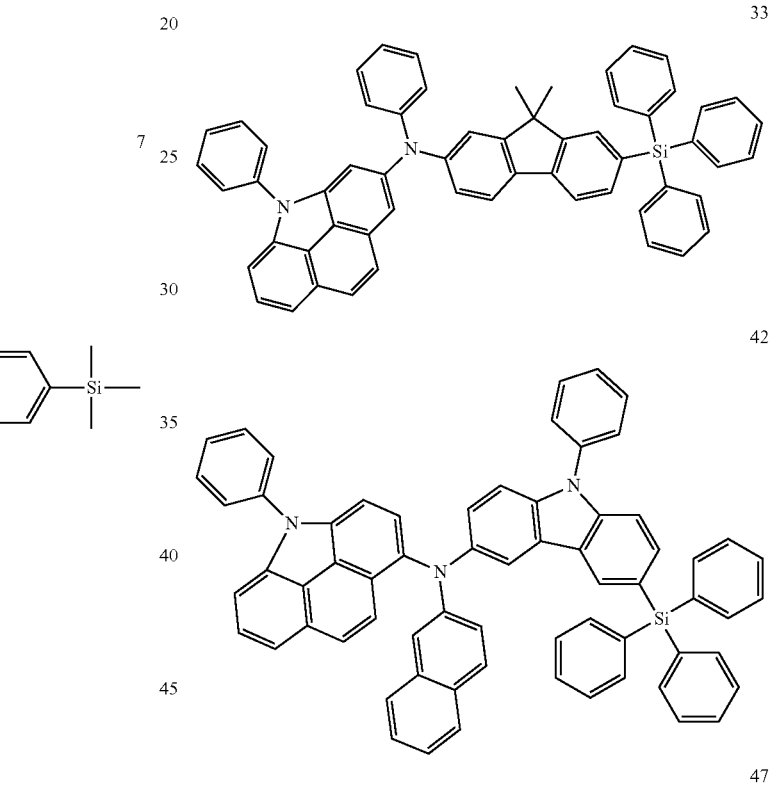
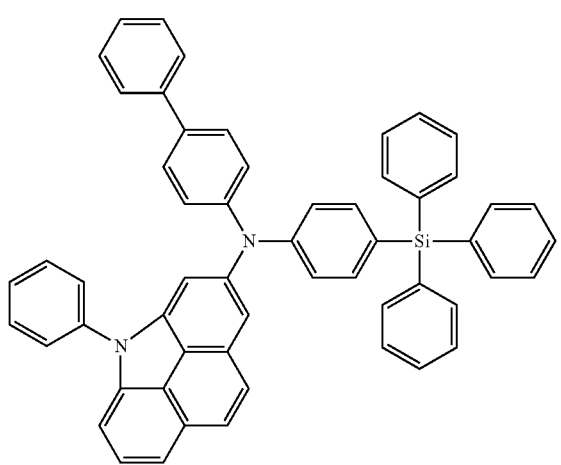

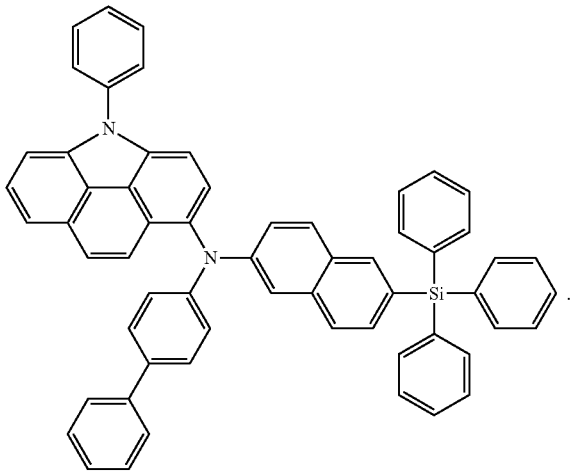

7. An organic light-emitting diode, comprising:
a first electrode;
a second electrode; and
an organic layer disposed between the first electrode and the second electrode, the organic layer including the heterocyclic compound as claimed in claim 1.

8. The organic light-emitting diode as claimed in claim 7, wherein the organic layer is a hole injection layer (HIL), a hole transport layer (HTL), or a functional layer having both hole injection and hole transport capabilities.

9. The organic light-emitting diode as claimed in claim 7, wherein the organic layer includes an emission layer (EML), and, optionally, one or more of an electron injection layer (EIL), an electron transport layer (ETL), a functional layer having both electron injection and electron transport capabilities, a hole injection layer (HIL), a hole transport layer (HTL), or a functional layer having both hole injection and hole transport capabilities, the EML further including an anthracene-based compound, an arylamine-based compound, or a styryl-based compound.

10. The organic light-emitting diode as claimed in claim 7, wherein the organic layer includes an emission layer (EML), and, optionally, one or more of an electron injection layer (EIL), an electron transport layer (ETL), a functional layer having both electron injection and electron transport capabilities, a hole injection layer (HIL), a hole transport layer (HTL), or a functional layer having both hole injection and hole transport capabilities, wherein the EML includes at least one layer of a red EML, a green EML, a blue EML, or a white EML that includes a phosphorescent compound.

11. The organic light-emitting diode as claimed in claim 10, wherein the hole injection layer (HIL), the hole transport layer (HTL), or the functional layer having both hole injection and hole transport capabilities includes a charge-generating material.

12. The organic light-emitting diode as claimed in claim 11, wherein the charge-generating material is a p-dopant.

13. The organic light-emitting diode as claimed in claim 12, wherein the p-dopant is a quinone derivative.

14. The organic light-emitting diode as claimed in claim 12, wherein the p-dopant is a metal oxide.

15. The organic light-emitting diode as claimed in claim 12, wherein the p-dopant is a cyano group-containing compound.

16. The organic light-emitting diode as claimed in claim 7, wherein the organic layer includes an electron transport layer (ETL), and the ETL includes a metal complex.

17. The organic light-emitting diode as claimed in claim 16, wherein the metal complex is a Li complex.

18. The organic light-emitting diode as claimed in claim 16, wherein the metal complex is lithium quinolate (LiQ) or Compound 203:

<Compound 203>

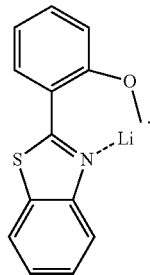

19. The organic light-emitting diode as claimed in claim 7, wherein the organic layer is formed using a wet process.

20. A flat panel display device, comprising the organic light-emitting diode as claimed in claim 7, wherein the first electrode of the organic light-emitting diode is electrically connected to a source electrode or a drain electrode of a thin-film transistor.

* * * * *